US012019803B2

(12) United States Patent
Everman et al.

(10) Patent No.: US 12,019,803 B2
(45) Date of Patent: Jun. 25, 2024

(54) METHODS AND SYSTEMS FOR INDIVIDUALIZED CONTENT MEDIA DELIVERY

(71) Applicant: GMECI, LLC, Beavercreek, OH (US)

(72) Inventors: Bradford R. Everman, Haddonfield, NJ (US); Brian Scott Bradke, Brookfield, VT (US)

( * ) Notice: Subject to any disclaimer, the term of this patent is extended or adjusted under 35 U.S.C. 154(b) by 0 days.

(21) Appl. No.: 17/959,689

(22) Filed: Oct. 4, 2022

(65) Prior Publication Data

US 2023/0031383 A1 Feb. 2, 2023

Related U.S. Application Data

(63) Continuation of application No. 17/387,491, filed on Jul. 28, 2021.

(51) Int. Cl.
*G06F 3/01* (2006.01)
*G09B 5/06* (2006.01)
(Continued)

(52) U.S. Cl.
CPC ............... *G06F 3/015* (2013.01); *G09B 5/06* (2013.01); *A61B 5/486* (2013.01); *G06F 18/254* (2023.01)

(58) Field of Classification Search
CPC .... G06F 3/015; G06F 18/254; G06F 2218/12; A61B 5/486; A61B 5/16; G09B 5/06; G09B 5/065; G09B 5/02; G09B 5/08; G09B 5/00; G09B 7/00; G09B 7/02; G09B 7/08; G06N 20/00
See application file for complete search history.

(56) References Cited

U.S. PATENT DOCUMENTS 8,620,419 B2 12/2013 Rotenberg et al.
10,120,413 B2 11/2018 Aimone et al.
(Continued)

FOREIGN PATENT DOCUMENTS

KR 20160109913 9/2016

OTHER PUBLICATIONS

Carroll et al., Automatic Detection of Learner Engagement Using Machine Learning and Wearable Sensors, Mar. 31, 2020.

*Primary Examiner* — Xuemei Zheng
(74) *Attorney, Agent, or Firm* — Caldwell Intellectual Property Law

(57) ABSTRACT

Aspects relate to systems and methods for individualized content media delivery. An exemplary system includes a sensor configured to detect a biofeedback signal as a function of a biofeedback of a user, a display configured to present content to the user, and a computing device configured to control an environmental parameter for an environment surrounding the user as a function of the biofeedback signal, wherein controlling the environmental parameter additionally includes generating an environmental machine-learning model as a function of an environmental machine-learning algorithm, training the environmental machine-learning model as a function of an environmental training set, wherein the environmental training set comprises biofeedback inputs correlated to environmental parameter outputs and generating the environmental parameter as a function of the biofeedback signal and the environmental machine-learning model.

20 Claims, 14 Drawing Sheets

1200

Detect biofeedback signal — 1205

Present educational content — 1210

Generate an environmental machine-learning model — 1215

Train an environmental machine-learning model — 1220

Generate an environmental parameter — 1225

(51) Int. Cl.
*A61B 5/00* (2006.01)
*G06F 18/25* (2023.01)

(56) References Cited

U.S. PATENT DOCUMENTS

| | | | |
|---|---|---|---|
| 10,347,148 | B2 | 7/2019 | Slivka et al. |
| 10,957,083 | B2 | 3/2021 | Du |
| 2007/0117081 | A1 | 5/2007 | Ford |
| 2013/0216989 | A1 | 8/2013 | Cuthbert |
| 2014/0255889 | A1 | 9/2014 | Grimes et al. |
| 2015/0351655 | A1 | 12/2015 | Coleman |
| 2016/0042648 | A1 | 2/2016 | Kothuri |
| 2017/0186331 | A1 | 6/2017 | Lawrenson et al. |
| 2019/0033914 | A1* | 1/2019 | Aimone ............... A61B 5/6821 |
| 2019/0282155 | A1 | 9/2019 | St Amant et al. |
| 2020/0135039 | A1 | 4/2020 | Karna et al. |
| 2020/0242952 | A1 | 7/2020 | Clinton et al. |
| 2020/0320890 | A1* | 10/2020 | Kumar Agrawal ..... G06F 3/015 |

* cited by examiner

METHODS AND SYSTEMS FOR INDIVIDUALIZED CONTENT MEDIA DELIVERY

CROSS-REFERENCE TO RELATED APPLICATIONS

This application is a continuation of Non-provisional application Ser. No. 17/387,491, filed on Jul. 28, 2021, and entitled "METHODS AND SYSTEMS FOR INDIVIDUALIZED CONTENT MEDIA DELIVERY," the entirety of which is incorporated herein by reference.

FIELD OF THE INVENTION

The present invention generally relates to the field of artificial intelligence and machine-learning processes. In particular, the present invention is directed to methods and system for individualized education content media delivery.

BACKGROUND

Presently digital content has not been more common. Massive open online courses (MOOCs) and pandemic-inspired online education has changed the ways content is presented to many learners. However not all learn best with these new forms of education.

SUMMARY OF THE DISCLOSURE

In an aspect a method of individualized content media delivery includes detecting, using at least a sensor, at least a biofeedback signal as a function of a biofeedback of a user, presenting, using at least a display, content to the user, and controlling, using at least a computing device, at least an environmental parameter for an environment of the user as a function of the at least a biofeedback signal, wherein controlling the at least an environmental parameter further includes an environmental machine-learning model as a function of an environmental machine-learning algorithm, training the environmental machine-learning model as a function of an environmental training set, wherein the environmental training set comprises biofeedback inputs correlated to environmental parameter outputs, and generating an output to an environmental component as a function of the at least a biofeedback signal and the environmental machine-learning model.

In another aspect, a system for individualized content media delivery includes at least a sensor configured to detect at least a biofeedback signal as a function of a biofeedback of a user, at least a display configured to present content to the user, and at least a computing device configured to control at least an environmental parameter for an environment of the user as a function of the at least a biofeedback signal, wherein controlling the at least an environmental parameter includes generating an environmental machine-learning model as a function of an environmental machine-learning algorithm, training the environmental machine-learning model as a function of an environmental training set, wherein the environmental training set comprises biofeedback inputs correlated to environmental parameter outputs, and generating an output to an environmental component as a function of the at least a biofeedback signal and the environmental machine-learning model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for individualized content delivery. In an embodiment, content is delivered to a user in such a manner that aspects related to display of the content and/or aspects related to an environment in which the user is located may be controlled according to sensed biofeedback of the user.

Aspects of the present disclosure can be used to change display and/or environmental parameters based upon at least a biofeedback of user. In some cases, at least a biofeedback of user may be indicative of user state. A user state may include a classification of how receptive a user is to presentation of educational materials. For instance, at least a biofeedback may be detected that shows a user is attentive or inattentive at any given time, in response a display parameter associated with presentation of content may be modulated (e.g., volume of audio may be changer, speed of presentation of content may be changed, and the like.) and/or an environmental parameter associated with an environment in which the user is located may be modulated (e.g., room lighting may be changed, room temperature may be changed, and the like). Aspects of the present disclosure can be used to increase an educational quantity and/or rate of a user. Aspects of the present disclosure can also be used to increase an educational quality of a user (i.e., improve user's retention of educational materials). This is so, at least in part, because detection of at least a biofeedback of a user allows system to make inferences about a user's learning experience.

Aspects of the present disclosure allow for improved learning at increased rates. Exemplary embodiments illustrating aspects of the present disclosure are described below in the context of several specific examples.

Figure 1:
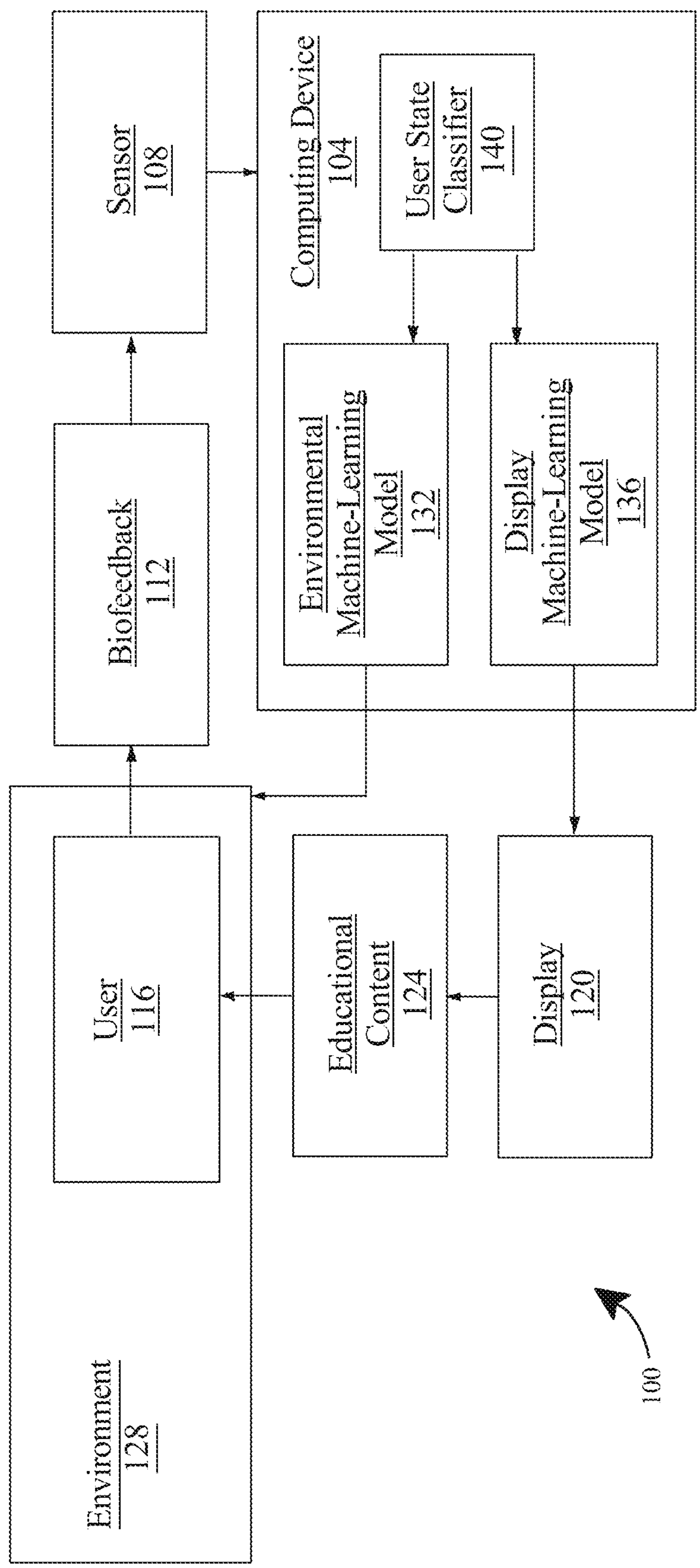
FIG. 1 is a block diagram illustrating a system for individualized content delivery.

Referring now to FIG. 1, an exemplary embodiment of a system 100 for individualized content delivery is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. computing device 104 may include a single computing device operating independently, or may include two or more computing device operating in concert, in parallel, sequentially or the like; two or more computing devices may be included together in a single computing device or in two or more computing devices. computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. computing device 104 may include but is not limited to, for example, a computing device or cluster of computing devices in a first location and a second computing device or cluster of computing devices in a second location. computing device 104 may include one or more computing devices dedicated to data storage, security, distribution of traffic for load balancing, and the like. computing device 104 may distribute one or more computing tasks as described below across a plurality of computing devices of computing device, which may operate in parallel, in series, redundantly, or in any other manner used for distribution of tasks or memory between computing devices. computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, system 100 may include at least a sensor 108. As used in this disclosure, a "sensor" is any device that is configured to detect a phenomenon and transmit a signal according to the detected phenomenon. For instance in some embodiments, a sensor 108 may be configured to detect a biofeedback 112 of a user 116. As used in this disclosure, a "biofeedback" is biological phenomenon that is indicative of a response. For example, a biofeedback may in some cases be a biological phenomenon that is indicative of a user's attentiveness. An instructive example of a biofeedback is that of a "poker tell." A poker tell is a biological phenomenon that manifests as a response to a poker hand; in some cases, a poker tell may indicate to other attentive poker players a quality of the hand of the player with the poker tell. A poker tell is provided as an example of a biofeedback, because it manifests subconsciously and in response to something (a player considering his poker hand). As with the poker tell example, in some cases, a biofeedback may be detected visually. Alternatively or additionally, in some cases, a biofeedback may be detected through alternative means, such as without limitation such as by way of any sensor described in this application, for example with reference to FIGS. 2-7. In some cases, at least a sensor 108 may be configured to detect at least a biofeedback signal as a function of a biofeedback 112 of a user 116. As used in this disclosure, a "biofeedback signal" is at least an element of data associated with detection of biofeedback. As used in this disclosure, a "signal" is a representation of at least an element of data. A signal may include an analog signal, a digital signal, an electrical signal, an optical signal, and the like. In some cases, a signal may be represented according to one or more protocols, for example without limitation universal asynchronous receiver-transmitter (UART), serial communication protocols, parallel communication protocols, and/or Ethernet protocols.

In some cases, at least a sensor 108 may perform one or more signal processing steps on a biofeedback signal. For instance, sensor 108 may analyze, modify, and/or synthesize a biofeedback signal in order to improve the signal, for instance by improving transmission, storage efficiency, and/or signal to noise ratio. Exemplary methods of signal processing may include analog, continuous time, discrete time, digital, nonlinear, and statistical. Analog signal processing may be performed on non-digitized or analog signals. Exemplary analog processes may include passive filters, active filters, additive mixers, integrators, delay lines, compandors, multipliers, voltage-controlled filters, voltage-controlled oscillators, and phase-locked loops. Continuous-time signal processing may be used, in some cases, to process signals which vary continuously within a domain, for instance time. Exemplary non-limiting continuous time processes may include time domain processing, frequency domain processing (Fourier transform), and complex frequency domain processing. Discrete time signal processing may be used when a signal is sampled non-continuously or at discrete time intervals (i.e., quantized in time). Analog discrete-time signal processing may process a signal using the following exemplary circuits: sample and hold circuits, analog time-division multiplexers, analog delay lines and analog feedback shift registers. Digital signal processing may be used to process digitized discrete-time sampled signals. Commonly, digital signal processing may be performed by a computing device or other specialized digital circuits, such as without limitation an application specific integrated circuit (ASIC), a field-programmable gate array (FPGA), or a specialized digital signal processor (DSP). Digital signal processing may be used to perform any combination of typical arithmetical operations, including fixed-point, floating-point, real-valued, and/or complex-valued multiplication and addition. Digital signal processing may additionally operate circular buffers and lookup tables. Further non-limiting examples of algorithms that may be performed according to digital signal processing techniques include fast Fourier transform (FFT), finite impulse response (FIR) filter, infinite impulse response (IIR) filter, and adaptive filters such as the Wiener and Kalman filters. Statistical signal processing may be used to process a signal as a random function (i.e., a stochastic process), utilizing statistical properties. For instance, in some embodiments, a signal may be modeled with a probability distribution indicating noise, which then may be used to reduce noise in a processed signal. In some cases, biofeedbacks 112 may be found (for instance through machine-learning processes described below) to correlate with certain levels of user performance. As used in this disclosure, "user performance" is an ability of a user to accomplish a given task, for example retain information within delivered content or a task unrelated to the delivered content. In some cases, user performance may be quantitatively represented by way of a performance metric. As used in this disclosure, a "performance metric" is a measure of user performance. Non-limiting examples of performance metric include results on a test or quiz, quantified performance of a duty or job function, and/or achievement of certain physical and mental objectives. In some cases, one or more machine-learning processes in this disclosure may be calibrated and/or trained using performance metrics, for example performance metrics correlated to biofeedbacks 112, display parameters, and/or environmental parameters for an individual user, a cohort of users, or a population of users.

With continued reference to FIG. 1, system 100 may include a display 120 configured to present content 124 to user 116. As used in this disclosure, a "display" is a visual projection device, such as a computer screen, a television, a projector and the like; in some cases, a display may comprise an audio-visual display and thereby may additionally include at least an audio transducer (e.g., speakers). Exemplary non-limiting displays 120 include liquid crystal displays, cathode ray tube displays, light emitting diode displays, organic light emitting diode displays, quantum dot displays, micro-electromechanical system (MEMS) projector, virtual reality headset, head mounted display, and the like. As described in this disclosure, "content" is any media (e.g., visual and/or audio) which contains information intended to be communicated to an audience. Exemplary content includes course material, lectures, laboratory experiments, and the like. Content may take a form of a document, slide show, spreadsheet, diagram, video, audio, interactive media, and the like. In some additional embodiments, system may be used with a live instructor (i.e., teacher, professor, trainer, supervisor, and the like), for example taking place of a display 120 or being presented by way of display 120. In some cases, content may be used for professional training, scholastic education, military training, physical training, satisfying one's curiosity, sport's training, self-help, therapy, meditation, mindfulness training, and the like. In some additional embodiments, content may include material interacted with by a subject, for example in service of a job or task. As an example, content may include security camera footage and a subject viewing the content may include security personnel. In another non-limiting embodiment, content may include interactive content, for example a control interface for an unmanned aerial vehicle (UAV) and subject interacting with the content may include a UAV pilot. In some cases, content may include a representation of a live environment, such as in the cases of the UAV pilot and the security personnel. Another such example is an application in which content represents air traffic control communication and subject interacting with the content is an air traffic controller. Content may be delivered substantially with or without a display. For example, content may be delivered through audio or through a live scene (e.g., live presenter).

With continued reference to FIG. 1, computing device may be configured to control at least an environmental parameter for an environment 128 surrounding user 116. As used in this disclosure, an "environmental parameter" is a controllable characteristic of an environment. As used in this disclosure, an "environment" is a physical area within which as user may be located, for instance while being presented content. Environmental parameters may relate to one or more characteristics of an environment, for example without limitation, illumination of the environment, temperature of the environment, humidity of the environment, sound (e.g., background and/or white noise) of the environment, and the like. An environmental parameter may include, without limitation, any environmental phenomenon to which a person may be exposed and/or which may affect health, attention, energy, and/or any other attribute and/or state of a person that may be detected, measured, or otherwise determined using biofeedback as described above. An environmental parameter may include, without limitation, ambient temperature, humidity, intensity and/or spectra of electromagnetic radiation including without limitation radiofrequency radiation, ultraviolet, visible, and/or infrared light, airflow, intensity and/or spectral makeup of sound, and/or any other parameter and/or combination of parameters that may occur to persons skilled in the art upon reviewing the entirety of this disclosure. Further embodiments describing environmental parameters and/or adjustment thereof are described in further detail below.

In some cases, computing device 104 may control at least an environmental parameter as a function of at least a biofeedback. For instance, in some cases, controlling environmental parameter may include generating an environmental machine-learning model 132 as a function of an environmental machine-learning algorithm; training the environmental machine-learning model 132 as a function of an environmental training set, wherein the environmental training set comprises biofeedback inputs correlated to environmental parameter outputs; and generating the at least an environmental parameter as a function of the at least a biofeedback signal and the environmental machine-learning model 132. As used in this disclosure, an "environmental machine-learning model" is a machine-learning model that takes as input at least a biofeedback and outputs at least an environmental parameter. Environmental machine-learning model 132 may include any machine-learning model described in this disclosure. As used in this disclosure, an "environmental machine-learning algorithm" is a machine-learning algorithm that is used to generate an environmental machine-learning model 132. Environmental machine-learning algorithm may include any machine-learning algorithm and/or process described in this disclosure. As used in this disclosure, an "environmental training set" is training data that is used to train environmental machine-learning model. According to some embodiments, environmental training set may include biofeedback inputs correlated to performance metric and/or environmental parameter outputs. According to some other embodiments, environmental training set may include biofeedback and or performance metric inputs correlated to environmental parameter outputs. Environmental training set may include any training set and/or training data described in this disclosure.

With continued reference to FIG. 1, in some cases, environment 128 may include one or more environmental devices. As used in this disclosure, an "environmental device" is a device that may modify an aspect of environment 128, for instance according to environmental parameter. In some cases, environmental device may include a "smart device," an Internet of Things (IoT) device, and/or a network enabled device. In some cases, environmental device may include a network enabled light (i.e., "smart light"). An exemplary non-limiting network enabled light includes Philips Hue™ lights from Koninklijke Philips N.V of Amsterdam, Netherlands. In some cases, environmental device may include a network enabled thermostat (i.e., "smart thermostat"). Exemplary non-limiting network enabled thermostats include Ecobee3™ from Ecobee Inc. of Toronto, Ontario, Canada and Nest™ Learning Thermostat from Alphabet, Inc. of Mountain View, California, U.S.A. In some cases, environmental device may include a network enabled speaker (i.e., "smart speaker"). An exemplary network enabled speaker includes Sonos Roam™ from Sonos, Inc. of Santa Barbara, California, U.S.A. At least an environmental device may be communicative with computing device 104. In some embodiments, at least an environmental device may be in direct wired communication with computing device 104, for instance without limitation by way of an Ethernet connection and/or a controller area network (CAN). Alternatively or additionally, in some cases, at least an environmental device may be in communication with computing device by way of indirect or direct wireless connection. Exemplary wireless connections include Wi-Fi, Zigbee (e.g., IEEE 802.15.4), Bluetooth, IPv6 over Low-Power Wireless Personal Area Networks (6LoWPAN), Cellular Networks, Wireless Sensor Networks (WSN), and the like. In some embodiments, one or more environmental devices may be controllable by computing device 104 by way of remote switches, relays, and the like. Exemplary remote switches and relays include without limitation solid state relays, network enabled electrical outlets (e.g., "smart plugs"), and the like.

Still referring to FIG. 1, in some embodiments, computing device 104 may additionally be configured to control at least a display parameter for at least a display 120. As used in this disclosure, a "display parameter" is a controllable characteristic of a display. Exemplary non-limiting display parameters may include visual parameters, audio parameters, and/or content parameters. As used in this disclosure, "audio parameters" is a controllable sound characteristic. Exemplary non-limiting audio parameters may include audio volume, audio mixer settings (e.g., treble, mid, bass, etc.), audio balance settings (e.g., left, right, etc.), audio fade settings (e.g., front, back, etc.), audio content settings (e.g., white noise, pink noise, etc.), and the like. In some cases, an audio parameter may include at least a change to audio content. For example, in some cases content may be augmented with audio intended to have an effect on a state of a user; for instance, a precipitous and loud sound may be inserted in order to increase alertness of a user. In some cases, display parameter may include a speed of presentation of content. For example, speed of presentation may be varied continuously and/or discretely from 0.5× to 3.0× speed of presentation. In some cases, a display parameter may include position of presentation of content, for instance within the display. In some embodiments, content may move within a display and according to a display parameter in response to biofeedback signal and in order to improve a user's receptiveness to the content. In some embodiments, speed of presentation may be controlled substantially proportional with a measured level of attentiveness of user, for example according to detected biofeedback. In some cases, computing device 104 may be configured to control at least a display 120 as a function of a biofeedback signal. For instance computing device 104 may control at least a display parameter by generating a display machine-learning model 136 as a function of a display machine-learning algorithm; training the display machine-learning model 136 as a function of a display training set, wherein the display training set comprises biofeedback inputs correlated to display parameter and/or performance metric outputs; and generating the at least a display parameter as a function of the at least a biofeedback signal and the display machine-learning model 136. As used in this disclosure, a "display machine learning-model" is a machine-learning model that takes as input at least a biofeedback and outputs at least a display parameter. In some embodiments, the display training set may include biofeedback and/or performance metric inputs correlated to display parameter outputs. Display machine-learning model 136 may include any machine-learning model described in this disclosure. As used in this disclosure, a "display machine-learning algorithm" is a machine-learning algorithm that is used to generate a display machine-learning model. Display machine-learning algorithm may include any machine-learning algorithm and/or process described in this disclosure. As used in this disclosure, a "display training set" is training data that is used to train display machine-learning model. According to some embodiments, display training set may include biofeedback inputs correlated to display parameter outputs. Display training set may include any training set and/or training data described in this disclosure.

Still referring to FIG. 1, in some embodiments, computing device 104 may be additionally configured to classify a user state, for instance by using a user state classifier 140. As used in this disclosure, a "user state" is a classification of a condition of a user; for instance, the condition may be related to the user's ability to absorb or otherwise learn for example from the content. Additionally, user state may be related to a user's ability to perform in some other capacity, for example in a physically strenuous activity. In some cases, user state may be classified according to a user's performance. For example, a user's performance may be related to a user's ability to retain communicated content, such as performance on a quiz on the communicated content. In some cases, a user's performance may be qualitatively and/or quantitatively determined according to other metrics, sensors, and/or measures. For example, a user's ability to succeed at any particular task may quantified and used as an input in any machine-learning process described in this disclosure. Exemplary non-limiting user states may include attentive, inattentive, focused, unfocused, and the like. In some case, computing device 104 may classify a user state as a function of biofeedback signal. For instance, computing device may be configured to classify a user state by generating a user state classifier 140 as a function of a user state machine-learning algorithm; training the user state classifier as a function of a user state training set; and classifying the user state as a function of the user state classifier and the biofeedback signal. As used in this disclosure, a "user state classifier" is a classifier that takes as input at least a biofeedback and outputs a user state. User state classifier 140 may include any machine-learning model and/or classifier described in this disclosure. As used in this disclosure, a "user state machine-learning algorithm" is a machine-learning algorithm that is used to generate a user state classifier 140. User state machine-learning algorithm may include any machine-learning algorithm and/or process described in this disclosure. As used in this disclosure, a "user state training set" is training data that is used to train user state classifier. According to some embodiments, user state training set may include biofeedback inputs. User training set may include any training set and/or training data as described in this disclosure. In some cases, computing device 104 may be additionally configured to selectively generate at least an environmental parameter as a function of the user state. For example, in some cases, environmental parameter may only be changed where user 116 is classified as being within an undesirable user state. Exemplary undesirable user states include any state of being that is non-conducive to learning from content 124, for example without limitation inattentiveness, drowsiness, anger, and the like. In some cases, computing device 104 is additionally configured to generate a confidence metric associated with classifying user state. As used in this disclosure, a "confidence metric" is a quantified score that is associated with a process, for example a fit or probability of a classification. Confidence metric may be generated and/or output from any machine-learning process as described in this disclosure, for example below.

Still referring to FIG. 1, in some cases, system 100 may be configured to communicate feedback characterizing quality of communication with user 116 to one or more users. In some cases, feedback characterizing quality of communication with user 116 may be referred to as a communication metric. Feedback characterizing quality of communication with user 116 may include any of biofeedback signal, user state, and/or confidence metric. In some cases, feedback may be provided to a different user than is being presented content. For example, in an exemplary embodiment where a class of students 116 is receiving content as part of an educational curriculum, a teacher or professor may have feedback characterizing quality of communication presented to her, for example by way of one or more displays. Feedback can be presented to a user 116 in real-time. Alternatively or additionally, feedback may be presented asynchronously. In some cases, feedback may be used to determine suitability of a subject for a particular task. For instance, in an exemplary embodiment where system 100 is being used with a UAV pilot, feedback may be used to determine if the UAV pilot needs to be replaced. It is not uncommon for the subjective opinions of those suffering sleep deprivation or exhaustion to not be representative. In some cases, system 100 may allow an objective determination (e.g., communication metric) to be made about a subject's ability to remain attentive to a task at hand.

Still referring to FIG. 1, in some cases system 100 may be used to store feedbacks characterizing quality of communication. For instance feedbacks may be stored to memory. Memory may include any memory component described in this disclosure. Stored feedbacks, in some cases, may be retrieved and analyzed. Analysis may be performed using any method described in this disclosure, including without limitation machine-learning processes. Stored feedbacks may be used to determine trends within the data. In some cases, feedbacks may be aggregated, for example added, multiplied, averaged, or the like. Aggregated feedbacks may include feedbacks from multiple users 116, for instance without limitation multiple users engaged with the same content. Alternatively or additionally, aggregated feedbacks may include feedbacks from substantially only one user, for instance without limitation one user 116 as she engages with a plurality of different contents over time. In some cases, feedbacks characterizing quality of communication of content may be normalized, for instance by way of statistical methods, such as averaging. In some cases, normalized feedbacks may be used as an objective measure of how a content was received or engaged with by a user 116 or by a plurality of users 116. In some cases, normalized feedbacks may be compared, for example without limitation to determine a quality of a first presentation compared to a second presentation.

Figure 2:
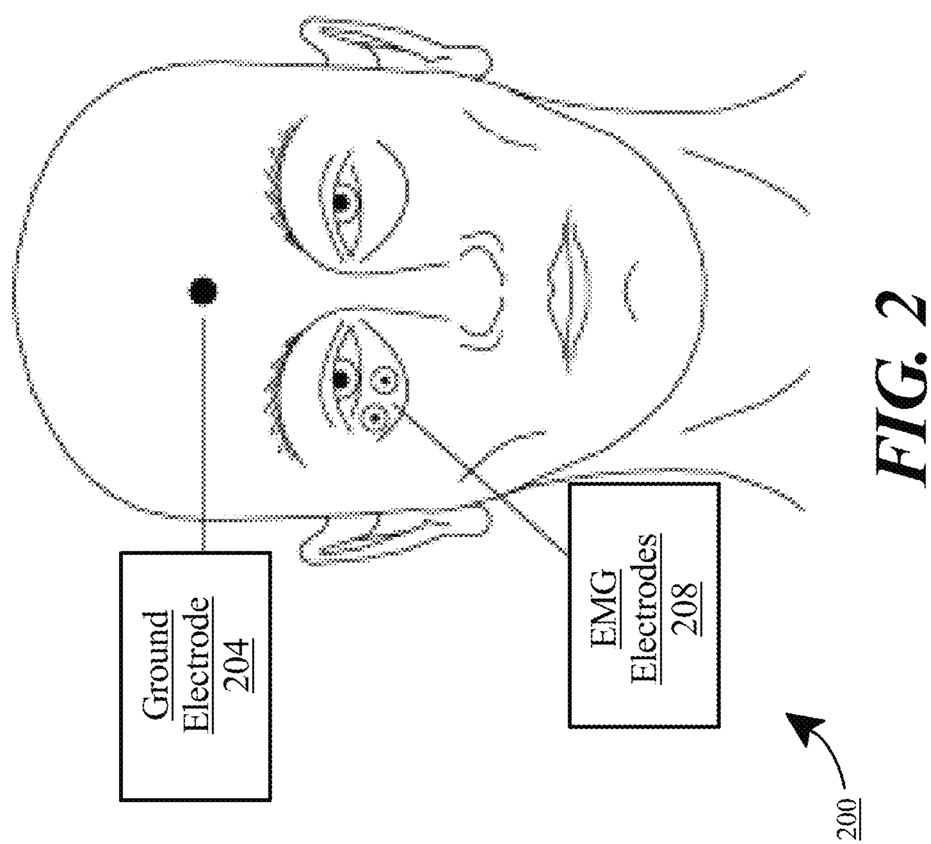
FIG. 2 illustrates exemplary placement of an electromyography sensor.

In some embodiments at least a sensor 108 may include an electromyography sensor. Referring now to FIG. 2 an exemplary EMG sensor 200 is illustrated. In some cases, electromyography (EMG) may be an electrodiagnostic medicine technique for evaluating and recording electrical activity produced by skeletal muscles. EMG may be performed using an instrument called an electromyograph to produce a record called an electromyogram. An electromyograph may detect electric potential generated by muscle cells, for instance when these cells are electrically or neurologically activated. Resulting electromyographic signals can be analyzed to detect medical abnormalities, activation level, or recruitment order, or to analyze the biomechanics of human or animal movement. In some cases, EMG may also be used as middleware in gesture recognition towards allowing input of physical action to a computing device or as a form of human-computer interaction. In some cases, an EMG sensor 200 may be located about an eye of a user and used to detect eye movements and/or blinks, for instance through detection of electrical activity of extraocular muscles. An EMG sensor 200 may include at least a ground electrode 204 and at least an EMG electrode 208. In some cases, a ground electrode 204 may be placed substantially away from an eye and/or extraocular muscles. In some cases, a ground electrode 204 may be electrically isolated (i.e., floating), thereby allowing detection of muscular electrical activity relative the body rather than relative a ground or other reference. In some cases, EMG signals may be substantially made up of superimposed motor unit action potentials (MUAPs) from several motor units (e.g., muscles). EMG signals can be decomposed into their constituent MUAPs. MUAPs from different motor units tend to have different characteristic shapes, while MUAPs recorded by the same electrode from the same motor unit are typically similar. Notably MUAP size and shape depend on where the electrode is located with respect to muscle fibers and so can appear different if an electrode 204, 208 moves position. EMG decomposition may involve any signal processing methods described in this disclosure, including those below.

With continued reference to FIG. 2, in some case EMG signal rectification may include translation of a raw EMG signal to a signal with a single polarity, for instance positive. In some cases, rectifying an EMG signal may be performed to ensure the EMG signal does not average to zero, as commonly a raw EMG signal may have positive and negative components. According to some embodiments, substantially two types of EMG signal rectification may be used full-wave and half-wave rectification. As used in this disclosure, "full-wave rectification" may add EMG signal below a baseline to the EMG signal above the baseline, thereby resulting in a conditioned EMG signal that is all positive. For example, if baseline of EMG signal is zero, full-wave rectification would be equivalent to taking an absolute value of the EMG signal. According to some embodiments, full-wave rectification may conserve substantially all of EMG signal energy for analysis. As used in this disclosure, "half-wave rectification" discards a portion of EMG signal below baseline. As a result of half-wave rectification, average of EMG signal may no longer be zero; therefore, an EMG signal conditioned by half-wave rectification can be used in further statistical analyses.

Still referring to FIG. 2, in some embodiments, EMG sensor 200 may be used to detect a gaze of user and/or the gaze of the user over time. As used in this disclosure, "gaze" is a direction a user is looking. As used in this disclosure "gaze vector" is a directional vector having a point located at a user's eye (e.g., pupil, retina, or the like) which represents a gaze of the user. In some cases, an EMG sensor 200 may be used to detect a gaze of a user over time and this information may be used as input for one or more machine-learning models described herein. For example, in some cases, user's whose gave is infrequently directed at display 120 may be found to have a relatively lower attentiveness than those whose gaze is fixed on the display 120. Alternatively or additionally, in some cases, a user's blink rate as detected by EMG sensor 200 may be used as an input for one or more machine-learning described herein. This is because, it also may be that users who blink more frequently are less attentive (e.g., drowsier) than those who blink less. For example, in an extreme case a user whose eyes are closed for prolonged periods of time may be found to be inattentive, perhaps even asleep; this condition may, in some cases, result in a change in an environmental parameter and/or a display parameter in order to wake up the user.

Referring again to FIG. 1, in some embodiments, similar gaze tracking and/or blink tracking functionality may be performed by a user facing camera and machine vision software. An exemplary machine vision camera that may be included as at least a sensor 108 is an OpenMV Cam H7 from OpenMV, LLC of Atlanta, Georgia, U.S.A. OpenMV Cam comprises a small, low power, microcontroller which allows execution of machine vision applications. OpenMV Cam comprises an ARM Cortex M7 processor and a 640×480 image sensor operating at a frame rate up to 150 fps. OpenMV Cam may be programmed with Python using a Remote Python/Procedure Call (RPC) library. OpenMV CAM may be used to operate image classification and segmentation models, such as without limitation by way of TensorFlow Lite; detection motion, for example by way of frame differencing algorithms; marker detection, for example blob detection; object detection, for example face detection; eye tracking; person detection, for example by way of a trained machine learning model; camera motion detection, for example by way of optical flow detection; code (barcode) detection and decoding; image capture; and video recording. In some cases, data from a machine vision camera 108 may be used as input for one or more machine-learning models which output one or more of an environmental parameter and a display parameter.

Still referring to FIG. 1, in some embodiments, a user's 116 position, habiliment, and/or posture may be detected by at least a sensor 108. For example, in some cases, a machine vision camera, like that described above may be employed to perform the detection. Alternatively or additionally, in some cases, range-imaging or 3D camera may be used for this purpose. An exemplary range-imaging camera that may be included as an at least a senser 108 is Intel® RealSense™ D430 Module, from Intel® of Mountainview, California, U.S.A. D430 Module comprises active infrared (IR) illumination and a stereoscopic camera, having global shutters and frame rate of up to 90 fps. D430 Module provide a field of view (FOV) of 85.2° (horizontal) by 58° (vertical) and an image resolution of 1280×720. Range-sensing camera may be operated independently by dedicated hardware, or, in some cases, range-sensing camera may be operated by a computing device. In some cases, range-sensing camera may include software and firmware resources (for execution on hardware, such as without limitation dedicated hardware or a computing device). D430 Module may be operating using software resources including Intel® Real Sense™ SDK 2.0, which include opensource cross platform libraries. In some cases, data from a range-imaging camera 108 may be used as input for one or more machine-learning models which output one or more of an environmental parameter and a display parameter.

Figure 3:
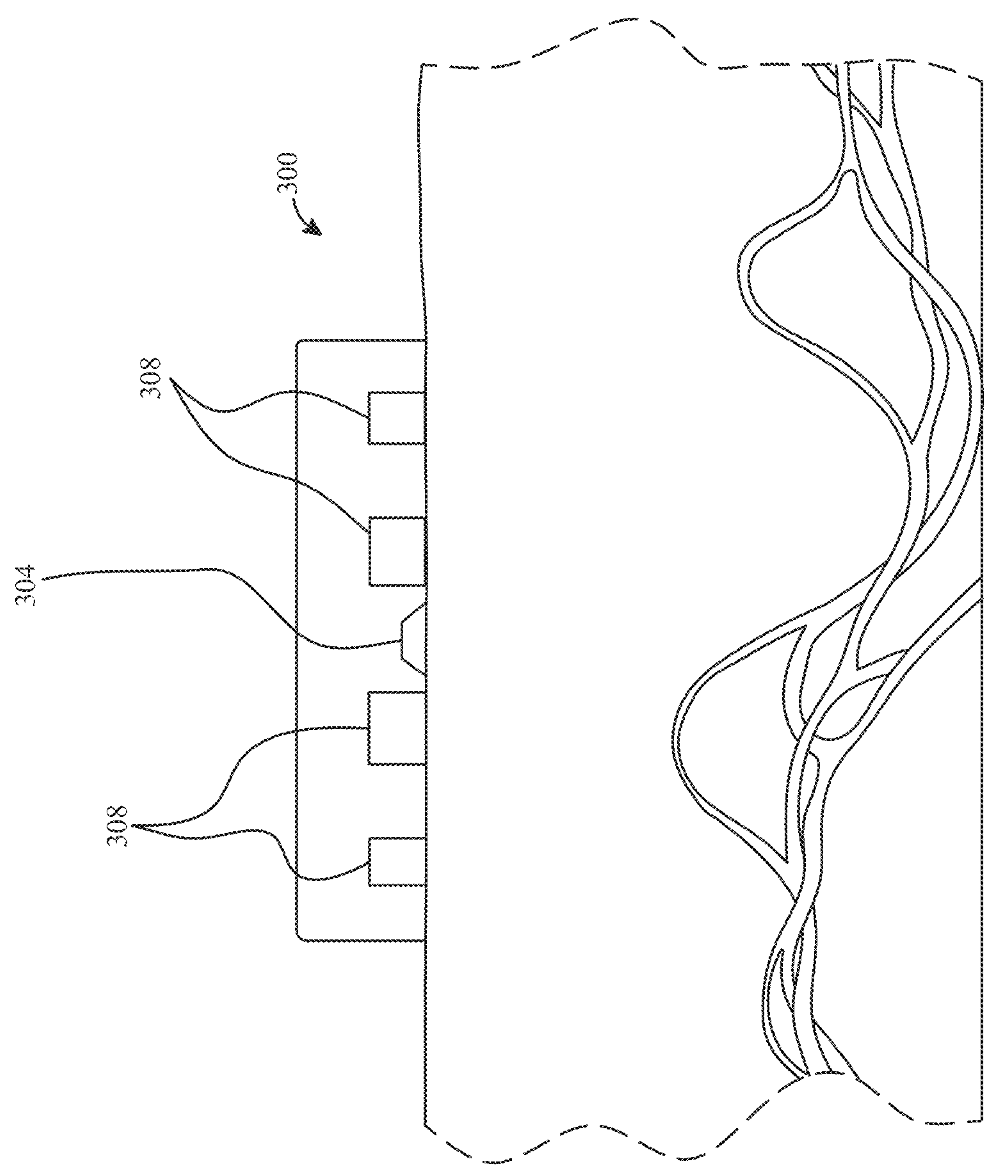
FIG. 3 is a schematic illustration of an exemplary embodiment of a near-infrared spectroscopy sensor.

Still referring to FIG. 1, at least a sensor 108 may include an optical sensor, which detects light emitted, reflected, or passing through human tissue. Optical sensor may include a near-infrared spectroscopy sensor (NIRS). A NIRS, as used herein, is a sensor that detects signals in the near-infrared electromagnetic spectrum region, having wavelengths between 780 nanometers and 2,500 nanometers. FIG. 3 illustrates an exemplary embodiment of a NIRS 300 against an exterior body surface, which may include skin. NIRS 300 may include a light source 304, which may include one or more light-emitting diodes (LEDs) or similar element. Light source 304 may, as a non-limiting example, convert electric energy into near-infrared electromagnetic signals. Light source 304 may include one or more lasers. NIRS 300 may include one or more detectors 308 configured to detect light in the near-infrared spectrum. Although the wavelengths described herein are infrared and near-infrared, light source 304 may alternatively or additionally emit light in one or more other wavelengths, including without limitation blue, green, ultraviolet, or other light, which may be used to sense additional physiological parameters. In an embodiment, light source may include one or more multi-wavelength light emitters, such as one or more multi-wavelength LEDs, permitting detection of blood-gas toxicology. Additional gases or other blood parameters so detected may include, without limitation CO2 saturation levels, state of hemoglobin as opposed to blood oxygen saturation generally. One or more detectors 308 may include, without limitation, charge-coupled devices (CCDs) biased for photon detection, indium gallium arsenide (InGaAs) photodetectors, lead sulfide (PbS) photodetectors, or the like. NIRS 300 may further include one or more intermediary optical elements (not shown), which may include dispersive elements such as prisms or diffraction gratings, or the like. In an embodiment, NIRS 300 may be used to detect one or more circulatory parameters, which may include any detectable parameter further comprises at least a circulatory parameter. At least a sensor 108 may include at least two sensors mounted on opposite sides of user's cranium. Further disclosure related to NIRS sensor 108 may be found in U.S. patent application Ser. No. 16/859,483, entitled "SYSTEMS AND METHODS FOR MEASURING PHYSIOLOGICAL PARAMETERS," the entirety of which is incorporated herein by reference.

Figure 4:
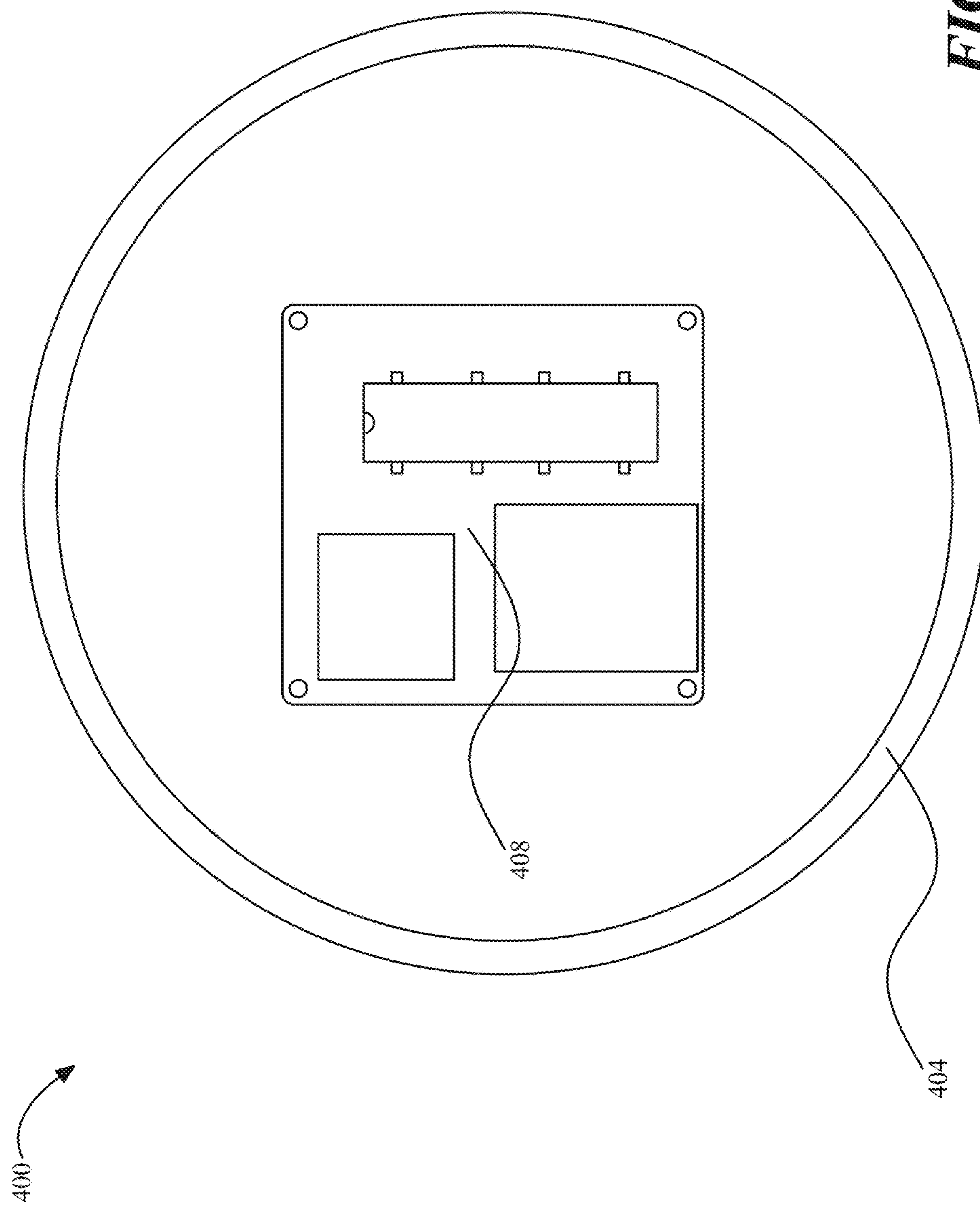
FIG. 4 is a schematic diagram illustrating an exemplary embodiment of a combined exhaled air and environmental gas sensor apparatus.

In some cases, at least a sensor 108 may include an exhaled gas sensor and/or an environmental gas sensor. Referring now to FIG. 4, combined exhaled air and environmental gas sensor 408 apparatus 400 for mobile respiratory equipment is illustrated. Apparatus 400 includes a housing 404, within which one or more electronic components are positioned. One or more electric components include a sensor 408. Housing 404 may be constructed of any suitable material or combination of materials, including without limitation metal, metal such as aluminum, titanium, steel, or the like, plant materials including bamboo and/or wood, polymer materials such as polycarbonate, polymethyl methacrylate, acrylonitrile butadiene styrene (ABS), or the like, synthetic fibers such as carbon fiber, silicon carbide fiber, metallic fiber, or the like, composite materials such as fiberglass, laminated fiberglass, plywood, or the like, or any combination of the above. Housing 404 may be manufactured in any suitable process including molding such as injection molding, additive manufacturing such as "three-dimensional printing" and/or stereolithography, subtractive processes such as machining, and/or any other process or combination of processes. Housing 404 may include a sensor-bearing surface 412 on or to which one or more electrical components including sensor 408 may be attached. Sensor-bearing surface 412 may be positioned opposite a port aperture as described in further detail below.

Figure 5B:
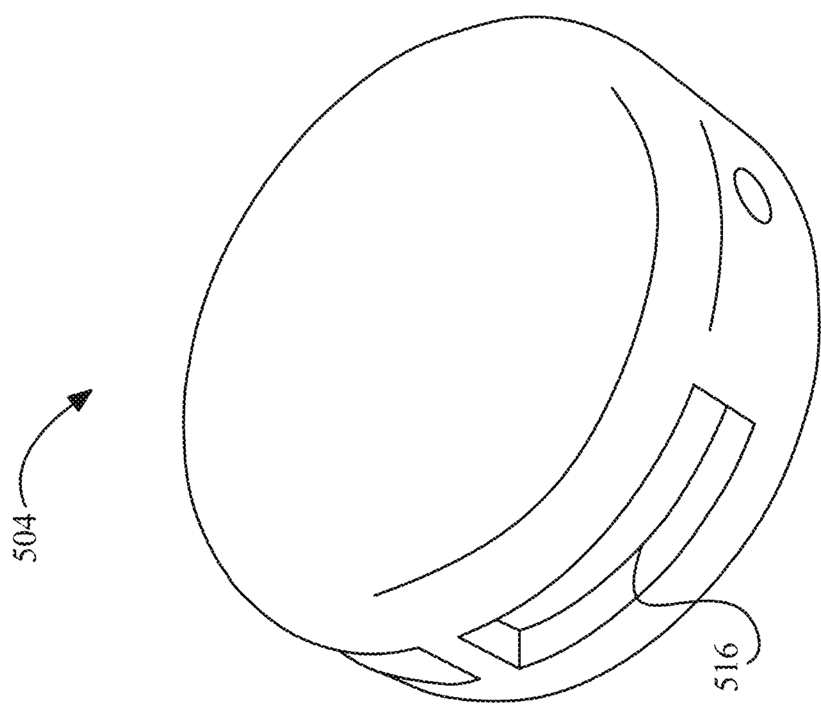
FIG. 5B is a schematic diagram illustrating an exemplary embodiment of a housing.
Figure 5A:
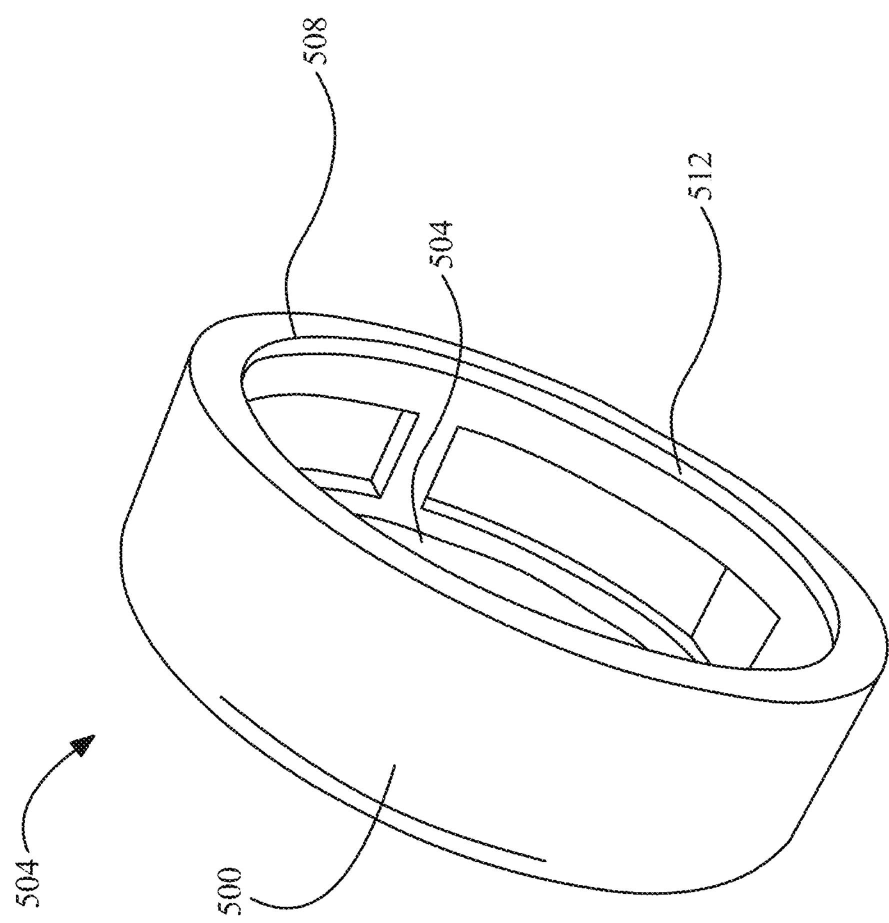
FIG. 5A is a schematic diagram illustrating an exemplary embodiment of a housing.

Referring now to FIG. 5A, a perspective view of an exemplary embodiment of a housing 404 is illustrated. Housing 404 may include an exterior surface 500, an interior surface 504, an interior space surrounded by interior surface 504, and one or more apertures. Housing 404 may have any suitable shape, including a shape of a cap to be placed over a respiratory exhaust port as described in further detail below. Housing 404 may be substantially cylindrical and may have one or more rounded edges. Housing 404 includes a port aperture 508. Port aperture 508 is an aperture that receives exhaled breath from a respiratory exhaust port as described in further detail below, admitting the exhaled breath into interior space of housing 404. Housing 404 further includes a connector 512, which may be located at port aperture 508. A "connector," as used in this disclosure, is a structural feature and/or component that affixes one aperture, opening, port, or the like to another in a way that permits flow of fluids such as liquid and/or gases to flow from one aperture, opening, port, or the like to another. Connector 512 is configured to attach port aperture 508 to exhaust port. Connector 512 may include, without limitation, a rim that fits and/or snaps over a feature of exhaust port to affix port aperture 508 thereto; connector 512 may alternatively or additionally include fastener, such as a bold or screw that inserts through a hole in housing 404 and screws into a reciprocally threaded hole in exhaust port. Connector 512 may include threading around port aperture 508 that engages reciprocal threading at exhaust port. Connector 512 may include and/or be combined with adhesives, sealants, or the like. Connector 512 may permit repeated detachment and reattachment or may effect a permanent connection between port aperture 508 and exhaust port. Persons skilled in the art, upon reviewing the entirety of this disclosure, will be aware of various alternative or additional structures and/or components that may be used for connector 512. Port aperture 508 may be located opposite sensor-bearing surface 412; for instance, sensor-bearing surface 412 may be located on interior surface 504 at a distal end of housing 404, while port aperture 508 may be located at a proximal end of housing 404.

Referring now to FIG. 5B, housing 404 includes at least an ambient aperture 516 connecting to an exterior environment. An "exterior environment," as used in this disclosure, means air that is exterior to an element of mobile respiratory equipment as described below; for instance, where mobile respiratory equipment is a respirator mask, exterior environment may include air outside of the mask and around a person wearing the mask, as opposed to air or gas between the mask and mouth or nose of the person. At least an ambient aperture 516 includes an opening connecting interior space to exterior environment. At least an ambient aperture 516 may permit air to travel freely between interior space and exterior environment.

Figure 6:
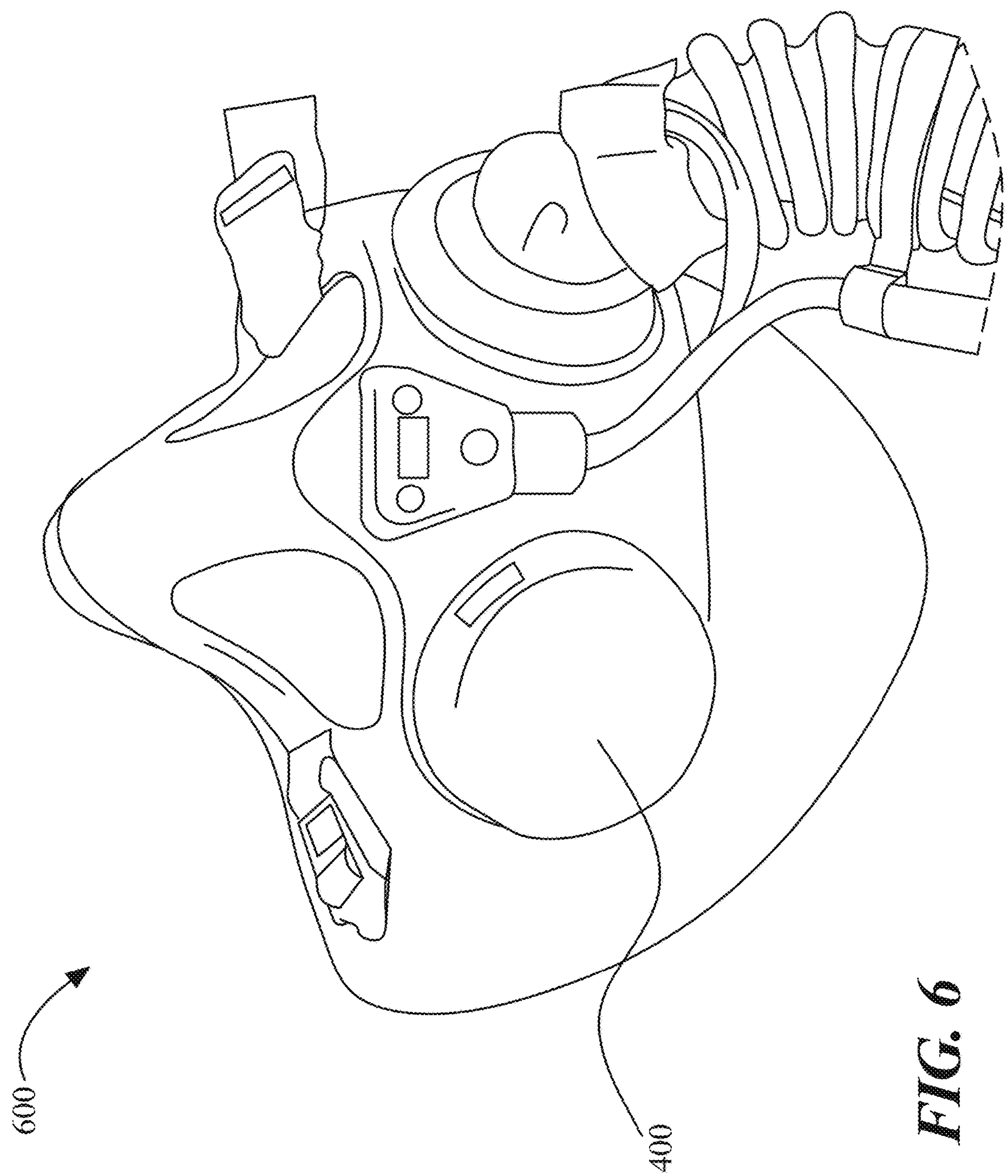
FIG. 6 is a schematic diagram illustrating an exemplary embodiment of a combined exhaled air and environmental gas sensor apparatus.

In an embodiment, and referring now to FIG. 6, housing 404 may be attached to an exhaust port of a mobile respiratory device 600. A "mobile respiratory device," as used herein, is a device worn on or about a face of a person, which aids in respiration, for instance when the person is in an environment where oxygen may be scarce or where other gases or particular matter such as carbon dioxide, carbon dioxide, toxic gases, droplets or fumes, or other elements that may interfere with respiration, and/or gases having ambient temperatures capable of harming a person when inhaled. Such an environment may include, without limitation, a cockpit of an aircraft such as a military aircraft, an artificially or naturally formed tunnel with an atmosphere that makes breathing difficult, such as an anoxic atmosphere, an atmosphere containing poisonous or otherwise problematic gases such as sulfur dioxide, carbon dioxide, carbon monoxide, or the like, a location at a high altitude such as a mountaintop, a location of a chemical spill and/or the like.

Still referring to FIG. 6, mobile respiratory device 600 may include, without limitation, a gas mask such as a cannister mask, a self-contained breathing apparatuses (SCBA) such as those used by firefighters, self-contained underwater breathing apparatuses (SCUBA), supplied-air respirators (SAR), particulate respirators, chemical cartridge respirators, powered air-purifying respirators (PAPRs), respirators included as part of a protective suit, airline respirators, N-95 or other NIOSH approved respirators, and/or other devices worn on and/or over and at least partially occluding the face to aid in respiration.

With continued reference to FIG. 6, an "exhaust port," as used in this disclosure, is an outlet that permits air exhaled by a user to escape from a mobile respiratory device 600. Exhaust port may include a valve such as a check-valve or other one-way valve to prevent air from entering a mobile respiratory device 600 from environment. Exhaust port may include, for instance, an exhale valve of a respirator mask or other such design. Exhaust port may also be an inlet port; for instance, air may be filtered while breathing in through the port and then exhaled, with or without filtering, via a valve at the same port. In operation, housing 404 with port aperture 508 and ambient aperture 516 may form a plenum in which exhaled and ambient air may flow freely by sensor 408, permitting sensation of both breath composition and environmental air composition. Further disclosure related to combined exhaled gas and environmental gas sensor 108 may be found in U.S. patent application Ser. No. 16/933,680, entitled "COMBINED EXHALED AIR AND ENVIRONMENTAL GAS SENSOR APPARATUS," the entirety of which is incorporated herein by reference.

Figure 7:
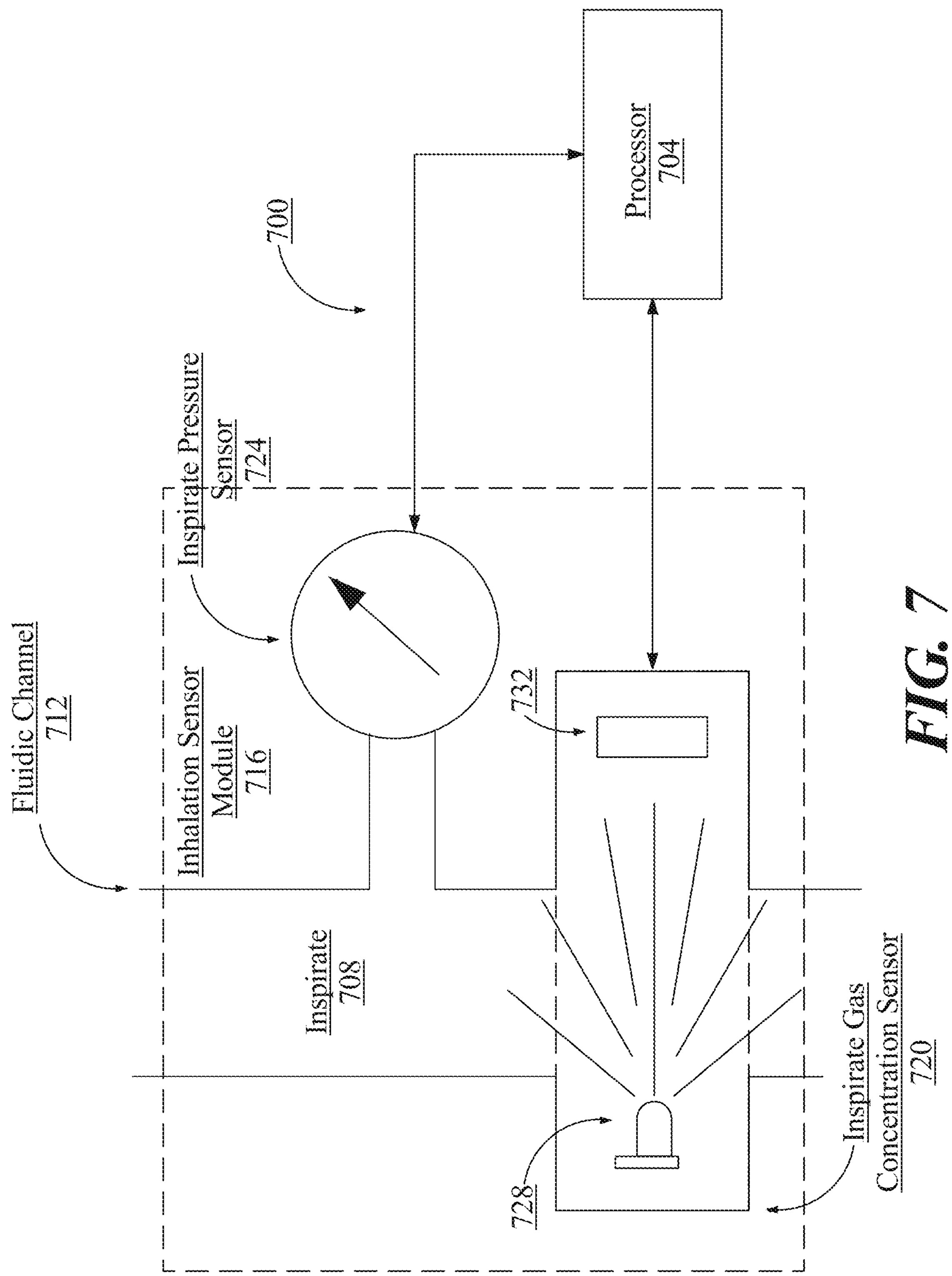
FIG. 7 is a block diagram illustrating an exemplary inhalation sensor module.

In some embodiments, at least a sensor 108 may include an inspirate sensor. Referring now to FIG. 7, an exemplary inspirate sensor 700 is illustrated. In some embodiments, inspirate sensor 700 may include a processor 704 for making determinations as a function of sensed parameters associated with at least an inspirate 708. in communication with an exemplary inhalation sensor module 708. In some cases, at least a portion of an at least an inspirate 708 is contained within a fluidic channel 712. An exemplary inhalation sensor module 716 is shown in fluid communication with fluidic channel 712. In some cases, inhalation sensor module may include at least a gas concentration sensor 720. In some cases, inhalation sensor module 716 may include at least an inspirate pressure sensor 724. Inspirate gas concentration sensor 720 may include any gas concentration sensor, for instance those described in this application. In some cases, inspirate gas concentration sensor 720 may include an optical gas concentration sensor. Non-limiting optical gas concentration sensors include infrared transmission and/or absorbance spectroscopy type sensors and fluorescence excitation type sensors. Commonly, an optical gas concentration sensor may include a radiation source 728 and a radiation detector 732. In some versions, radiation source 728 may include a light source 728 that may generate a light and illuminate at least a portion of at least an inspirate 708. Radiation source 728 may generate any of a non-limiting list of lights, including coherent light, non-coherent light, narrowband light, broadband light, pulsed light, continuous wave light, pseudo continuous wave light, ultraviolet light, visible light, and infrared light. In some cases, radiation source 728 may include an electromagnetic radiation source that may generate an electromagnetic radiation and irradiate at least a portion of at least an inspirate 708. Radiation source 728 may generate any of a non-limiting list of radiations including radio waves, microwaves, infrared radiation, optical radiation, ultraviolet radiation, X-rays, gamma-rays, and light. Non-limiting examples of radiation sources 728 include lasers, light emitting diodes (LEDs), light emitting capacitors (LECs), flash lamps, antennas, and the like. In some cases, radiation detector 732 may be configured to detect light and/or radiation that has interacted directly or indirectly with at least a portion of at least an inspirate 708. Non-limiting examples of radiation detectors 732 include photodiodes, photodetectors, thermopiles, pyrolytic detectors, antennas, and the like. In some cases, a radiation amount detected by radiation detector 732 may be indicative of a concentration of a particular gas in at least a portion of at least an inspirate 708. For example, in some exemplary embodiments, radiation source 728 may include an infrared light source operating at a wavelength about 4.6 μm and radiation detector may include a photodiode sensitive over a range encompassing 4.6 μm. An exemplary infrared light source may include an LED comprising InAsSb/InAsSbP heterostructures, for example LED46 from Independent Business Scientific Group (IBSG) of Saint Petersburg, Russia. An exemplary infrared detector may include a mercury cadmium telluride photodiode, for example UM-I-6 HgCdTe from Boston Electronics of Brookline, Massachusetts. In some cases, an amount of radiation at least a specific wavelength absorbed, scatter, attenuated, and/or transmitted may be indicative of a gas concentration.

With continued reference to FIG. 7, in some cases, inspirate concentration sensor 720 may include an infrared point sensor. An infrared (IR) point sensor may use radiation passing through a known volume of gas, for example at least an inspirate 708. In some cases, detector 732 may be configured to detect radiation after passing through gas at a specific spectrum. As energy from infrared may be absorbed at certain wavelengths, depending on properties of at least an inspirate 720. For example, carbon monoxide absorbs wavelengths of about 4.2-4.5 μm. In some cases, detected radiation within a wavelength range (e.g., absorption range) may be compared to a wavelength outside of the wavelength range. A difference in detected radiation between these two wavelength ranges may be found to be proportional to a concentration of gas present. In some embodiments, an infrared image sensors may be used for active and/or passive imaging. For active sensing, radiation source 728 may include a coherent light source (e.g., laser) which may be scanned across a field of view of a scene and radiation detector 732 may be configured to detect backscattered light at an absorption wavelength of a specific target gas. In some cases, radiation detector 732 may include an image sensor, for example a two-dimensional array of radiation sensitive devices, for example arranged as pixels. Passive IR imaging sensors may measure spectral changes at each pixel in an image and look for specific spectral signatures that indicate presence and/or concentration of target gases.

With continued reference to FIG. 7, in some cases, inspirate gas concentration sensor 720 may include an oxygen sensor. An exemplary oxygen sensor may include an electro-galvanic sensor. For example, an electro-galvanic oxygen sensor may be used to measure a concentration of oxygen within at least an inspirate 708. In some cases, an electro-galvanic oxygen sensor may include a lead/oxygen galvanic cell, within which oxygen molecules are dissociated and reduced to hydroxyl ions at a cathode. Hydroxyl ions may diffuse through an electrolyte and oxidize a lead anode. A current proportional to a rate of oxygen consumption may be generated when cathode and anode are electrically connected through a resistor. Current may be sensed by known current sensing methods, for example without limitation those described in this disclosure, to produce an electrical signal proportional to a concentration of oxygen, for example oxygen within at least an inspirate. Another exemplary oxygen sensor may include a lambda sensor, for example a zirconia sensor, a wideband zirconia sensor, and/or a titania sensor. A lambda sensor may be configured to sense a quantity of oxygen in a gas (e.g., at least an inspirate 708) relative another gas, for example air within an environment (e.g., cabin air) and transmit an analog voltage correlated to the sensed relative quantity of oxygen. Analog voltage transmitted by a lambda sensor may be processed by any data or signal processing methods discussed herein, for example through amplification and/or analog-to-digital conversion.

In another exemplary embodiment, inspirate concentration sensor 720 may include an optical sensor configured to sense oxygen concentration. In some cases, a chemical film is configured to be in contact with a gas (e.g., at least an inspirate 708). Chemical film may have fluorescence properties which are dependent upon presence and/or concentration of oxygen. Radiation detector 732 may be positioned and configured, such that it is in sensed communication with chemical film. Radiation source 728 may irradiate and/or illuminate chemical film with radiation and/or light having properties (e.g., wavelength, energy, pulse duration, and the like) consistent with exciting fluorescence within the chemical film. In some cases, fluorescence may be at a maximum when there is no oxygen present. For example, oxygen molecules may collide with chemical film and quench photoluminescence resulting from fluorescent excitation. A number of $O_2$ molecules colliding with chemical film may be correlated with a concentration of oxygen within a gas (e.g., inspirate 708). Fluorescence properties as sensed by optical detector 732 may therefore be related to oxygen concentration. Fluorescence properties may include emission duration, fluorescence energy, and the like. In some cases, detected optical signal (fluorescence) to oxygen concentration may not be linear. For instance, an optical oxygen sensor may be most sensitive at low oxygen concentration; that is, sensitivity decreases as oxygen concentration increases, following a known Stern-Volmer relationship. In some cases, an optical oxygen sensor is advantageous as substantially no oxygen may be consumed, during sensing. In some cases, planar optical oxygen sensors (i.e., optodes) may be used to detect a spatial distribution of oxygen concentrations over an area, for example as a two-dimensional image. Based on the same principle, radiation detector 732 may include a digital camera that may be used to capture fluorescence intensities over a specific area.

With continued reference to FIG. 7, inhalation sensor module 716 may include at least an inspirate pressure sensor 724, which is fluidic communication with at least an inspirate 708, for example by way of at least a fluidic channel 712. In some cases, at least an inspirate pressure sensor 716 may be configured to sense and transmit at least an inspirate pressure parameter as a function of a pressure of at least an inspirate 708. In some cases, inhalation pressure sensor 724 may include any type of pressure sensor described in this disclosure. Inhalation pressure sensor 724 may be a force collector type pressure sensor. Alternatively, in some case, inhalation pressure sensor 724 may be a pressure sensor type that does not use force collection. Further disclosure related to inhalation sensor 108 may be found in U.S. patent application Ser. No. 17/333,169, entitled "SYSTEMS AND METHODS FOR INSPIRATE SENSING TO DETERMINE A PROBABILITY OF AN EMERGENT PHYSIOLOGICAL STATE," the entirety of which is incorporated herein by reference.

Figure 8:
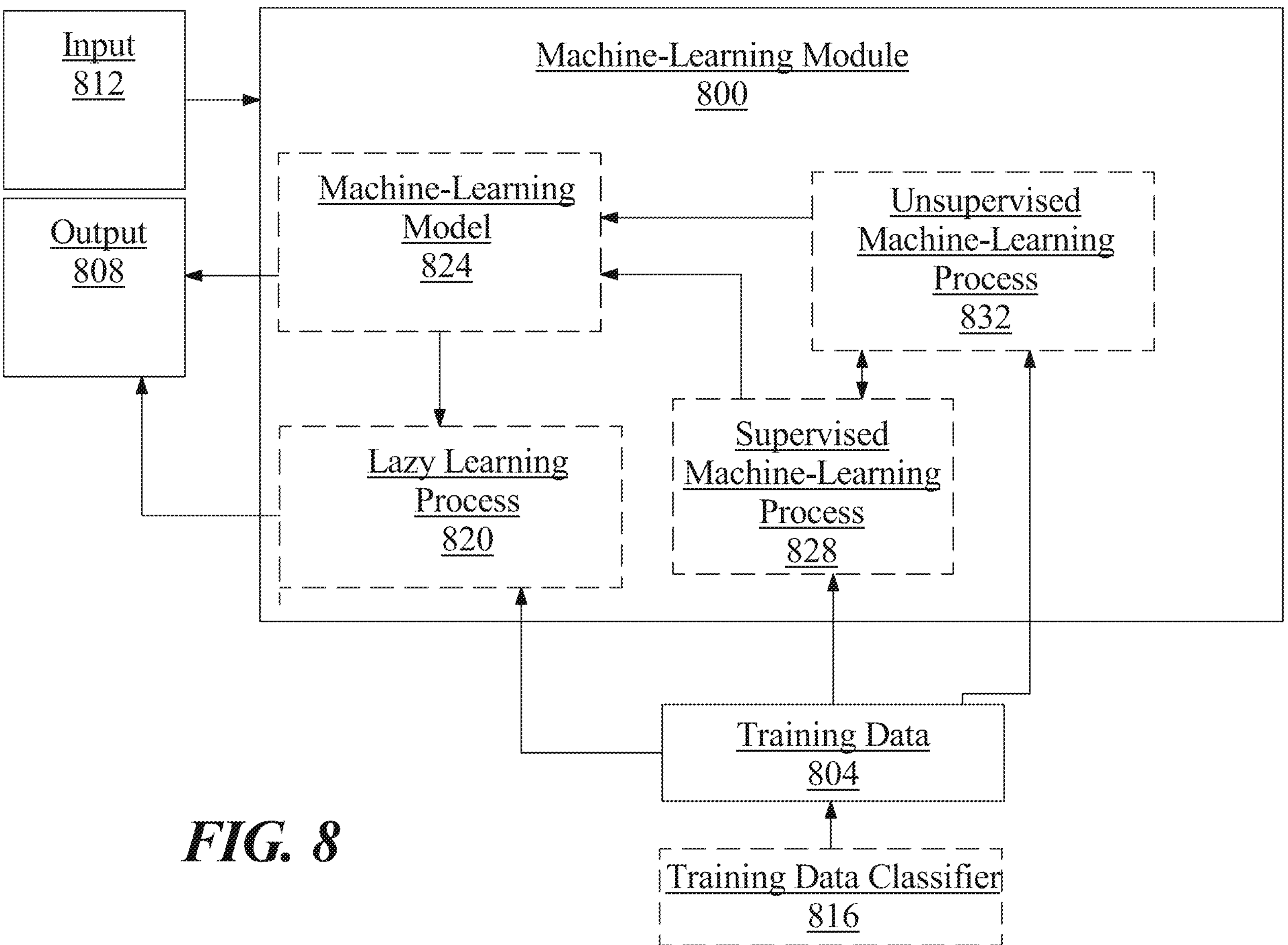
FIG. 8 is a block diagram of an exemplary machine-learning process.

Referring now to FIG. 8, an exemplary embodiment of a machine-learning module 800 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 804 to generate an algorithm that will be performed by a computing device/module to produce outputs 808 given data provided as inputs 812; this is in contrast to a non-machine learning software program where the commands to be executed are determined in advance by a user and written in a programming language.

Still referring to FIG. 8, "training data," as used herein, is data containing correlations that a machine-learning process may use to model relationships between two or more categories of data elements. For instance, and without limitation, training data 804 may include a plurality of data entries, each entry representing a set of data elements that were recorded, received, and/or generated together; data elements may be correlated by shared existence in a given data entry, by proximity in a given data entry, or the like. Multiple data entries in training data 804 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 804 according to various correlations; correlations may indicate causative and/or predictive links between categories of data elements, which may be modeled as relationships such as mathematical relationships by machine-learning processes as described in further detail below. Training data 804 may be formatted and/or organized by categories of data elements, for instance by associating data elements with one or more descriptors corresponding to categories of data elements. As a non-limiting example, training data 804 may include data entered in standardized forms by persons or processes, such that entry of a given data element in a given field in a form may be mapped to one or more descriptors of categories. Elements in training data 804 may be linked to descriptors of categories by tags, tokens, or other data elements; for instance, and without limitation, training data 804 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 8, training data 804 may include one or more elements that are not categorized; that is, training data 804 may not be formatted or contain descriptors for some elements of data. Machine-learning algorithms and/or other processes may sort training data 804 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 804 to be made applicable for two or more distinct machine-learning algorithms as described in further detail below. Training data 804 used by machine-learning module 800 may correlate any input data as described in this disclosure to any output data as described in this disclosure. As a non-limiting illustrative example biofeedback signals may be categorized according to user and/or user cohort. In some cases, a machine-learning model may need to be trained using training substantially from only one user. Alternatively or additionally, in some cases, training data may include biofeedback signals from a population of users.

Further referring to FIG. 8, training data may be filtered, sorted, and/or selected using one or more supervised and/or unsupervised machine-learning processes and/or models as described in further detail below; such models may include without limitation a training data classifier 816. Training data classifier 816 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 800 may generate a classifier using a classification algorithm, defined as a processes whereby a computing device and/or any module and/or component operating thereon derives a classifier from training data 804. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 8, machine-learning module 800 may be configured to perform a lazy-learning process 820 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 804. Heuristic may include selecting some number of highest-ranking associations and/or training data 804 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 8, machine-learning processes as described in this disclosure may be used to generate machine-learning models 824. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 824 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 824 may be generated by creating an artificial neural network, such as a convolutional neural network comprising an input layer of nodes, one or more intermediate layers, and an output layer of nodes. Connections between nodes may be created via the process of "training" the network, in which elements from a training data 804 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 8, machine-learning algorithms may include at least a supervised machine-learning process 828. At least a supervised machine-learning process 828, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include inputs and outputs as described above in this disclosure, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 804. Persons skilled in the art, upon reviewing the entirety of this disclosure, will be aware of various possible variations of at least a supervised machine-learning process 828 that may be used to determine relation between inputs and outputs. Supervised machine-learning processes may include classification algorithms as defined above.

Further referring to FIG. 8, machine learning processes may include at least an unsupervised machine-learning processes 832. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 8, machine-learning module 800 may be designed and configured to create a machine-learning model 824 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 8, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 9:
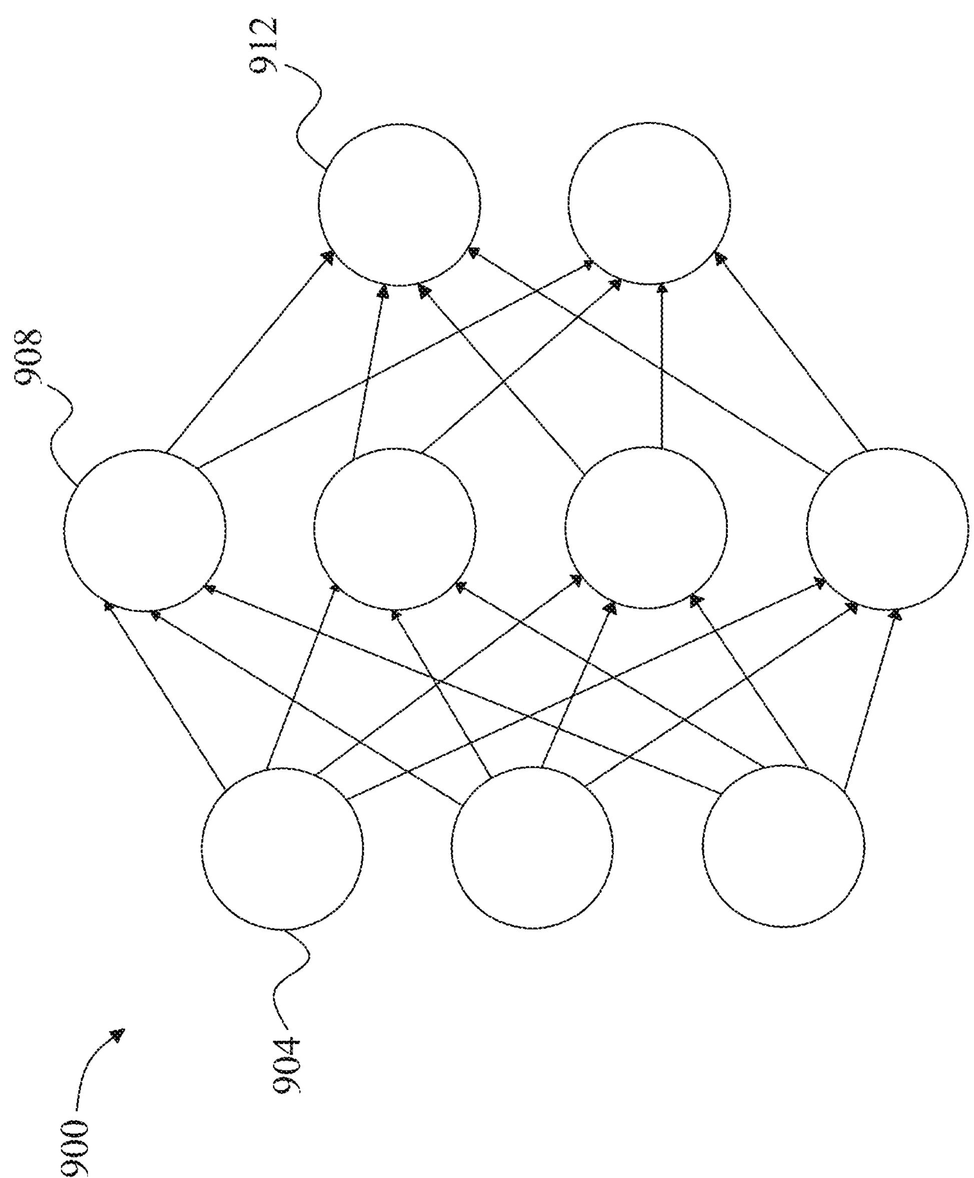
FIG. 9 is a schematic diagram of an exemplary embodiment of a neural network.

Referring now to FIG. 9 an exemplary embodiment of neural network 900 is illustrated. Neural network also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 904, one or more intermediate layers 908, and an output layer of nodes 912. Connections between nodes may be created via the process of "training" the network, in which elements from a training dataset are applied to input nodes 904, a suitable training algorithm (such as Levenberg-Marquardt, conjugate gradient, simulated annealing, or other algorithms) is then used to adjust the connections and weights between nodes in adjacent layers 908 of the neural network to produce the desired values at output nodes 912. This process is sometimes referred to as deep learning.

Figure 10:
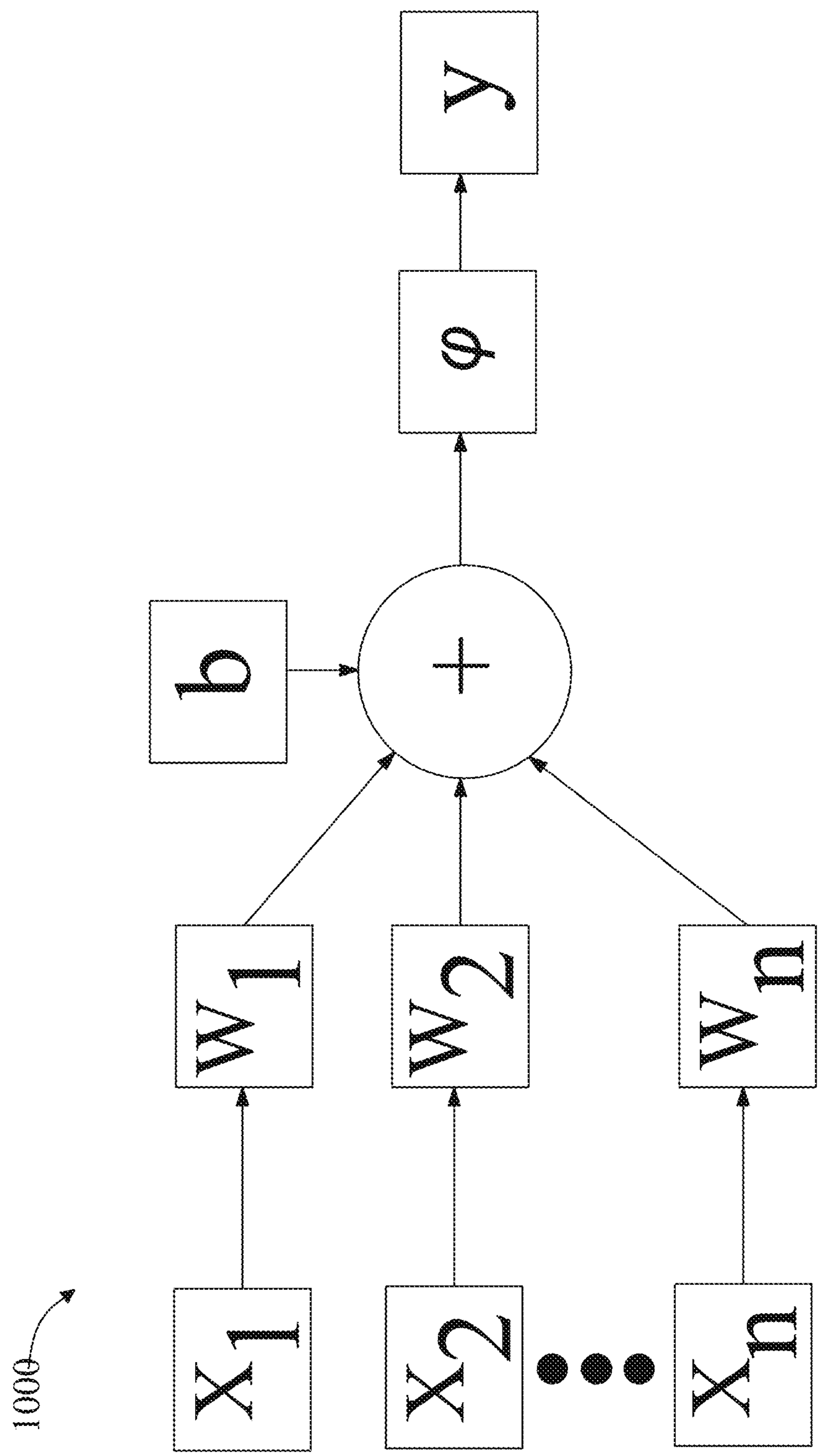
FIG. 10 is a schematic diagram of an exemplary embodiment of a node of a neural network.

Referring now to FIG. 10, an exemplary embodiment of a node 1000 of a neural network is illustrated. A node 1000 may include, without limitation a plurality of inputs $x_i$ that may receive numerical values from inputs to a neural network containing the node and/or from other nodes. Node 1000 may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function $\varphi$, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Still referring to FIG. 10, a neural network may receive biofeedbacks as inputs and output on or more of a display parameter and an environmental parameter. Alternatively or additionally in some cases, a neural network may receive biofeedback data as inputs and output confidence metric representing a probability of classification to a predetermined class, for instance user state, according to weights $w_i$ that are derived using machine-learning processes as described in this disclosure.

Referring again to FIG. 1, In some embodiments, computing device 104 may be configured to modify a training set in response to a biofeedback signal correlated to an environmental parameter or a display parameter; where the environmental parameter or the display parameter may represent an actual known occurrence that is related to a user state. For example, computing device 104 may, in some cases, retrain a machine-learning model, for instance environmental machine-learning model 132 and/or display machine-learning model 136, using a biofeedback signal correlated to a user state. In some embodiments, computing device 104 may be configured to classify at least one of a user state, an environmental parameter, and a display parameter and determine a confidence metric. For example, in some exemplary embodiments confidence metric may be a floating-point number within a prescribed range, such as without limitation 0 to 1, with each end of the prescribed range representing an extreme representation, such as without limitation substantially no confidence and substantially absolute confidence, respectively. In some cases, confidence output may represent a relationship between a result of filtering and/or classifying a user state. Confidence metric may be determined by one more comparisons algorithms, such as without limitation a fuzzy set comparison. For example, in some exemplary embodiments a fuzzy set comparison may be employed to compare a probabilistic outcome with a membership function derived to represent at least a threshold used for classification.

Figure 11:
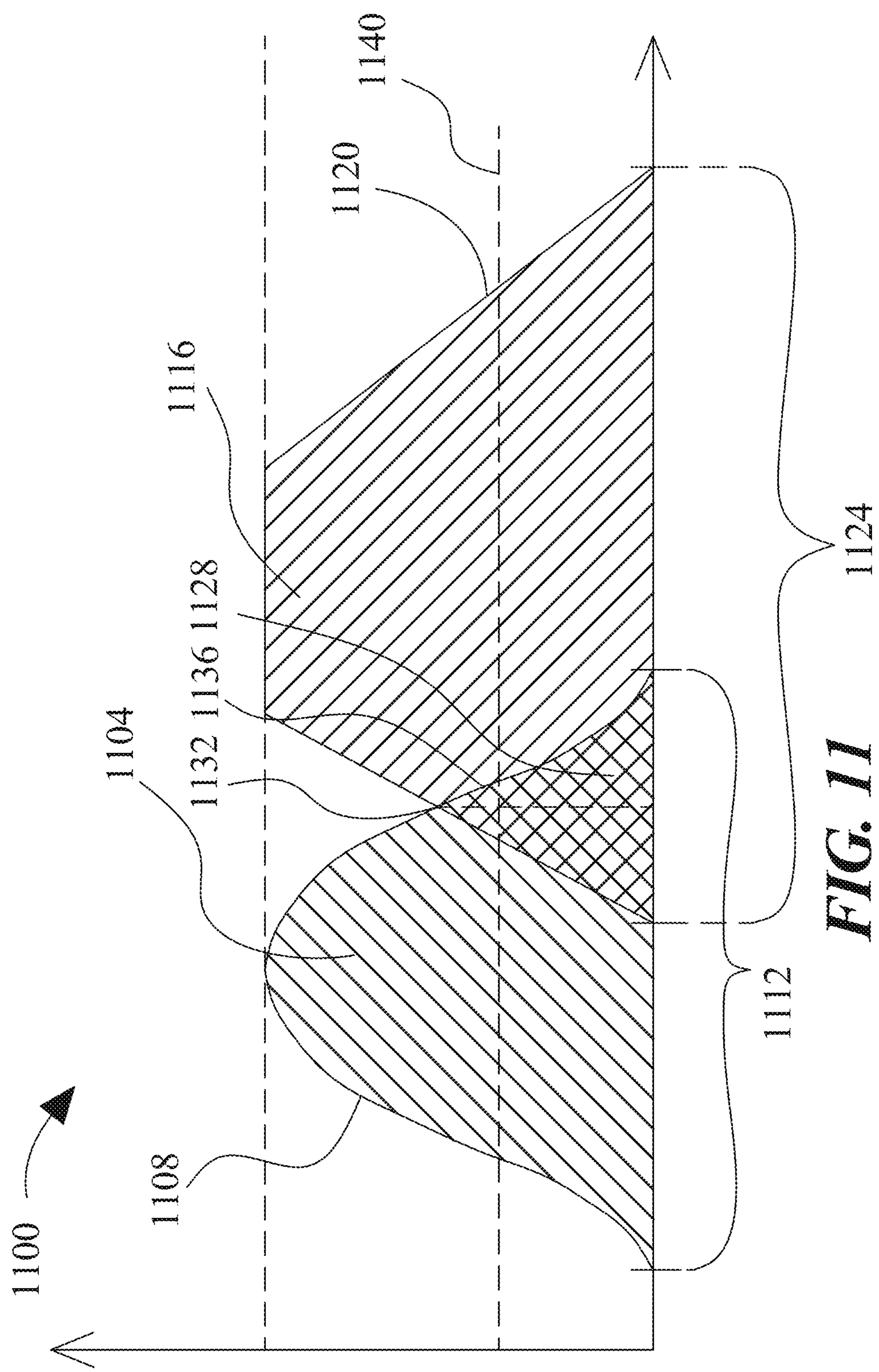
FIG. 11 is a graph representing an exemplary embodiment of a fuzzy set comparison.

Referring to FIG. 11, an exemplary embodiment of fuzzy set comparison 1100 is illustrated. A first fuzzy set 1104 may be represented, without limitation, according to a first membership function 1108 representing a probability that an input falling on a first range of values 1112 is a member of the first fuzzy set 1104, where the first membership function 1108 has values on a range of probabilities such as without limitation the interval [0,1], and an area beneath the first membership function 1108 may represent a set of values within first fuzzy set 1104. Although first range of values 1112 is illustrated for clarity in this exemplary depiction as a range on a single number line or axis, first range of values 1112 may be defined on two or more dimensions, representing, for instance, a Cartesian product between a plurality of ranges, curves, axes, spaces, dimensions, or the like. First membership function 1108 may include any suitable function mapping first range 1112 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \le x < b \\ \frac{c-x}{c-b}, \text{ if } b < x \le c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 11, first fuzzy set 1104 may represent any value or combination of values as described above, including output from one or more machine-learning models and biofeedback signals from sensor 108, a predetermined class, such as without limitation a user state (e.g., attentive, inattentive, and the like). A second fuzzy set 1116, which may represent any value which may be represented by first fuzzy set 1104, may be defined by a second membership function 1120 on a second range 1124; second range 1124 may be identical and/or overlap with first range 1112 and/or may be combined with first range via Cartesian product or the like to generate a mapping permitting evaluation overlap of first fuzzy set 1104 and second fuzzy set 1116. Where first fuzzy set 1104 and second fuzzy set 1116 have a region 1128 that overlaps, first membership function 1108 and second membership function 1120 may intersect at a point 1132 representing a probability, as defined on probability interval, of a match between first fuzzy set 1104 and second fuzzy set 1116. Alternatively or additionally, a single value of first and/or second fuzzy set may be located at a locus 1136 on first range 1112 and/or second range 1124, where a probability of membership may be taken by evaluation of first membership function 1108 and/or second membership function 4110 at that range point. A probability at 1128 and/or 1132 may be compared to a threshold 1140 to determine whether a positive match is indicated. Threshold 1140 may, in a non-limiting example, represent a degree of match between first fuzzy set 1104 and second fuzzy set 1116, and/or single values therein with each other or with either set, which is sufficient for purposes of the matching process; for instance, threshold may indicate a sufficient degree of overlap between an output from one or more machine-learning models and/or a biofeedback signal and a predetermined class, such as without limitation a user state, for combination to occur as described above. Alternatively or additionally, each threshold may be tuned by a machine-learning and/or statistical process, for instance and without limitation as described in further detail below.

Further referring to FIG. 11, in an embodiment, a degree of match between fuzzy sets may be used to classify a biofeedback signal with a user state. For instance, if a biofeedback signal has a fuzzy set matching a user state fuzzy set by having a degree of overlap exceeding a threshold, computing device 104 may classify the biofeedback signal as belonging to the user state. Where multiple fuzzy matches are performed, degrees of match for each respective fuzzy set may be computed and aggregated through, for instance, addition, averaging, or the like, to determine an overall degree of match.

Still referring to FIG. 11, in an embodiment, a biofeedback signal may be compared to multiple user state fuzzy sets. For instance, biofeedback signal may be represented by a fuzzy set that is compared to each of the multiple user state fuzzy sets; and a degree of overlap exceeding a threshold between the biofeedback signal fuzzy set and any of the multiple user state fuzzy sets may cause computing device 104 to classify the biofeedback signal as belonging to a user state. For instance, in one embodiment there may be two user state fuzzy sets, representing respectively an attentive state and an inattentive state. Attentive state may have an attentive state fuzzy set; inattentive state may have an inattentive state fuzzy set; and biofeedback signal may have a biofeedback fuzzy set. Computing device 104, for example, may compare a biofeedback fuzzy set with each of attentive state fuzzy set and inattentive state fuzzy set, as described above, and classify a biofeedback signal to either, both, or neither of attentive state or inattentive state. Machine-learning methods as described throughout may, in a non-limiting example, generate coefficients used in fuzzy set equations as described above, such as without limitation x, c, and σ of a Gaussian set as described above, as outputs of machine-learning methods. Likewise, biofeedback signal may be used indirectly to determine a fuzzy set, as biofeedback fuzzy set may be derived from outputs of one or more machine-learning models that take the biofeedback signal directly or indirectly as inputs.

Figure 12:
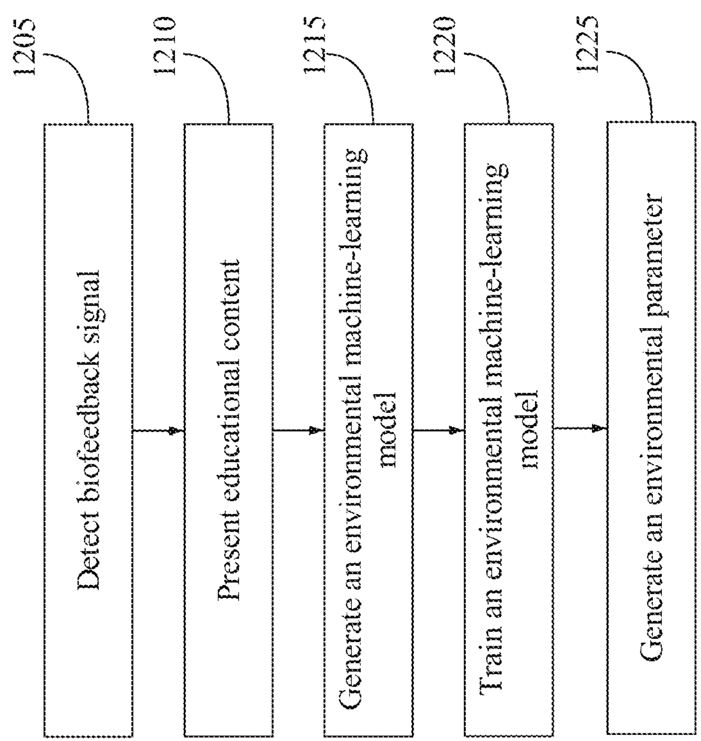
FIG. 12 is a flow diagram of an exemplary method of individualized content delivery.

Referring now to FIG. 12, an exemplary method 1200 of individualized content delivery is illustrated by way of a flow diagram. At step 1205, method 1200 may include detecting, using at least a sensor, at least a biofeedback signal as a function of a biofeedback of a user. Sensor may include any sensor described in this disclosure, for example with reference to FIGS. 1-11. Biofeedback signal may include any biofeedback signal described in this disclosure, for example FIGS. 1-11. Biofeedback may include any biofeedback described in this disclosure, for example FIGS. 1-11. User may include any user described in this disclosure, for example with reference to FIGS. 1-11.

With continued reference to FIG. 12, at step 1210, method 1200 may include presenting, using at least a display, content to user. Display may include any display described in this disclosure, for example with reference to FIGS. 1-11. In some embodiments, display may include an audio-visual display. Content may include any content described in this disclosure, for example with reference to FIGS. 1-11.

With continued reference to FIG. 12, method 1200 may include controlling, using at least a computing device, at least an environmental parameter for an environment surrounding user as a function of at least a biofeedback signal. Computing device may include any computing device described in this disclosure, for example with reference to FIGS. 1-11 and 10. Environmental parameter may include any environmental parameter described in this disclosure, for example with reference to FIGS. 1-11. Environment may include any environment described in this disclosure, for example with reference to FIGS. 1-11. In some cases, controlling at least an environmental parameter may additionally include step 1215, generating an environmental machine-learning model as a function of an environmental machine-learning algorithm. Environmental machine-learning model may include any machine-learning model described in this disclosure, for example with reference to FIGS. 1-11. Environmental machine-learning algorithm may include any machine-learning algorithm or machine-learning process described in this disclosure, for example with reference to FIGS. 1-11. In some cases, controlling at least an environmental parameter may additionally include step 1220, training environmental machine-learning model as a function of an environmental training set. Environmental training set may include any training set described in this disclosure, for example with reference to FIGS. 1-11. In some cases, environmental training set may include biofeedback inputs correlated to environmental parameter outputs. In some cases, controlling at least an environmental parameter may additionally include step 1225, generating at least an environmental parameter as a function of at least a biofeedback signal and environmental machine-learning model. In some embodiments, at least an environmental parameter may include a thermal parameter. In some embodiments, at least an environmental parameter may include a lighting parameter.

Still referring to FIG. 12, in some embodiments, method 1200 may additionally include controlling, using computing device, at least a display parameter for at least a display as a function of at least a biofeedback signal. Display parameter may include any display parameter described in this disclosure, for example with reference to FIGS. 1-11. In some cases, controlling at least a display parameter may additionally include generating a display machine-learning model as a function of a display machine-learning algorithm, training the display machine-learning model as a function of a display training set, wherein the display training set comprises biofeedback inputs correlated to display parameter outputs, and generating the at least a display parameter as a function of the at least a biofeedback signal and the display machine-learning model. Display machine-learning model may include any machine-learning model described in this disclosure, for example with reference to FIGS. 1-11. Display machine-learning algorithm may include any machine-learning algorithm or machine-learning process described in this disclosure, for example with reference to FIGS. 1-11. In some embodiments, at least a display parameter may include an audio parameter. In some embodiments, at least a display parameter may include a speed of presentation for content.

Still referring to FIG. 12, in some embodiments, method 1200 may additionally include classifying, using computing device, a user state as a function of the at least a biofeedback signal. User state may include any user state described in this disclosure, for example with reference to FIGS. 1-11. In some cases, classifying user state may additionally include generating a user state classifier as a function of a user state machine-learning algorithm; training the user state classifier as a function of a user state training set; and classifying the user state as a function of the user state classifier and the biofeedback signal. User state classifier may include any machine-learning model or classifier described in this disclosure, for example with reference to FIGS. 1-11. User state machine-learning algorithm may include any machine-learning algorithm or machine-learning process described in this disclosure, for example with reference to FIGS. 1-11. User state training set may include any training set or training data described in this disclosure, for example with reference to FIGS. 1-11. In some cases, generating at least an environmental parameter may additionally selectively generating the at least an environmental parameter as a function of user state. In some embodiments, user state may be associated with attentiveness. In some embodiments, method 1200 may additionally include generating, using computing device, a confidence metric associated with classifying the user state. Confidence metric may include any confidence metric described in this disclosure, for example with reference to FIGS. 1-11.

Referring again to FIG. 1, system 100 may be used in any number of applications, many non-limiting examples have been provided throughout this disclosure. In some embodiments, system 100 may be used to provide a practical improvement to online classes. Online classes have seen an increase in popularity and use since the Covid pandemic, forced most people to isolate. Students and teachers have been forced to learn and teach remotely, engaging with one another by way of computer, a display, and audio. As a result of this, many subtle cues between teachers and students have been lost. A good teacher (or presenter generally) will look to her students (or audience generally) for non-verbal signs of engagement. This signs can include a raised eyebrow at a contentious moment of the course, a laugh at a presenter's joke, and the like. Many of these interpersonal feedbacks are obfuscated by current online teaching platforms. As a result of this, ambiguity arises over how much of a class students are receiving, and many teachers have found teaching remotely more difficult and less rewarding. In some exemplary embodiments, system 100 is used to improve upon this difficulty and provide a feedback characterizing quality of communication with one or more students 116 to a teacher. This feedback, in some cases, may be considered a metric of communication. In some cases, metric of communication may be presented to teacher through any means, including color coding, gauges, and the like. In some cases, a teacher will be presented with a metric of communication for each student with a color code (e.g., red representing poor communication, yellow representing moderate communication, and green representing good communication) with or without a numerical value. Teacher may then detect from this which students are engaged, and which are not. In some cases, teacher may be presented with an aggregated metric of communication for a group of students. For example, an aggregated metric of communication may communicate how well an entire class is receiving instruction from teacher.

In another exemplary embodiment, system 100 may be used with real-time content, for example a live presenter (no display). In this cases system 100 may adjust audio of presentation as well as environmental parameters.

In yet another exemplary embodiment, system 100 may be used to identify a user. For example, in some cases, system 100 may detect and/or confirm an identity of an individual user. System 100 may determine and/or confirm an identity of an individual user by using at least a biofeedback 112 and/or a user state. In some cases, at least a biofeedback 112 may be used as an input to at least a machine-learning process (e.g., machine-learning model) that is configured to identify an individual user as a function of at least a biofeedback 112 (e.g., image of the user) and or user state. In some cases, machine-learning model may be trained using training data that includes inputs including representative biofeedbacks correlated with individual user identities. A user-identifying machine-learning process may include any machine-learning process described in this disclosure, including without limitation supervised machine-learning processes, unsupervised machine-learning processes, and classifiers. In some exemplary applications, system 100 may identify an individual user prior to, during, and/or after completion of content delivery. System 100 may continuously and/or periodically identify an individual user. System 100 may periodically identify an individual user in order to maintain proof that the individual has not changed and is the individual user for which the content is intended. In one application, system 100 may be used to ensure that an individual user is the one receiving intended content during an examination, such as without limitation a remote scholastic aptitude test (SAT). As described throughout this disclosure and continuing with the SAT exemplary application, the system 100 may confirm not only a user's identity, but also her level of attention and/or engagement during the test. Although described in reference to an SAT test, system's 100 ability to continuously detect and/or confirm identity of a user may be useful in other applications to ensure that sensitive content is being delivered only to an intended audience.

In still another exemplary embodiment, system 100 may be used in conjunction with one or more other systems capable of determining and/or quantifying physical performance. For example, a user may be engaged in a physically strenuous activity (in addition to or instead of a mentally challenging activity). Physically strenuous activity may have certain metrics of performance, which are measured. For instance, where a physically strenuous activity includes a treadmill, performance metrics may include rate of the treadmill, incline of the treadmill, and the like. Alternatively or additionally, where physically strenuous activity includes a weight, performance metric may include number of repetitions, number of sets, mass of the weight, and the like. In some cases, system 100 may take as input a performance metric of a physically strenuous activity. Alternatively or additionally, a performance metric of a physically strenuous activity may include amount of time on-duty or in a state of wakefulness. System 100 may determine correlations and/or predictions based upon one or more of performance metrics, biofeedbacks, user state, environmental parameters, and/or display parameters, for example by using any machine-learning process described above in this disclosure, for example with reference to FIGS. 1-11.

Figure 13:
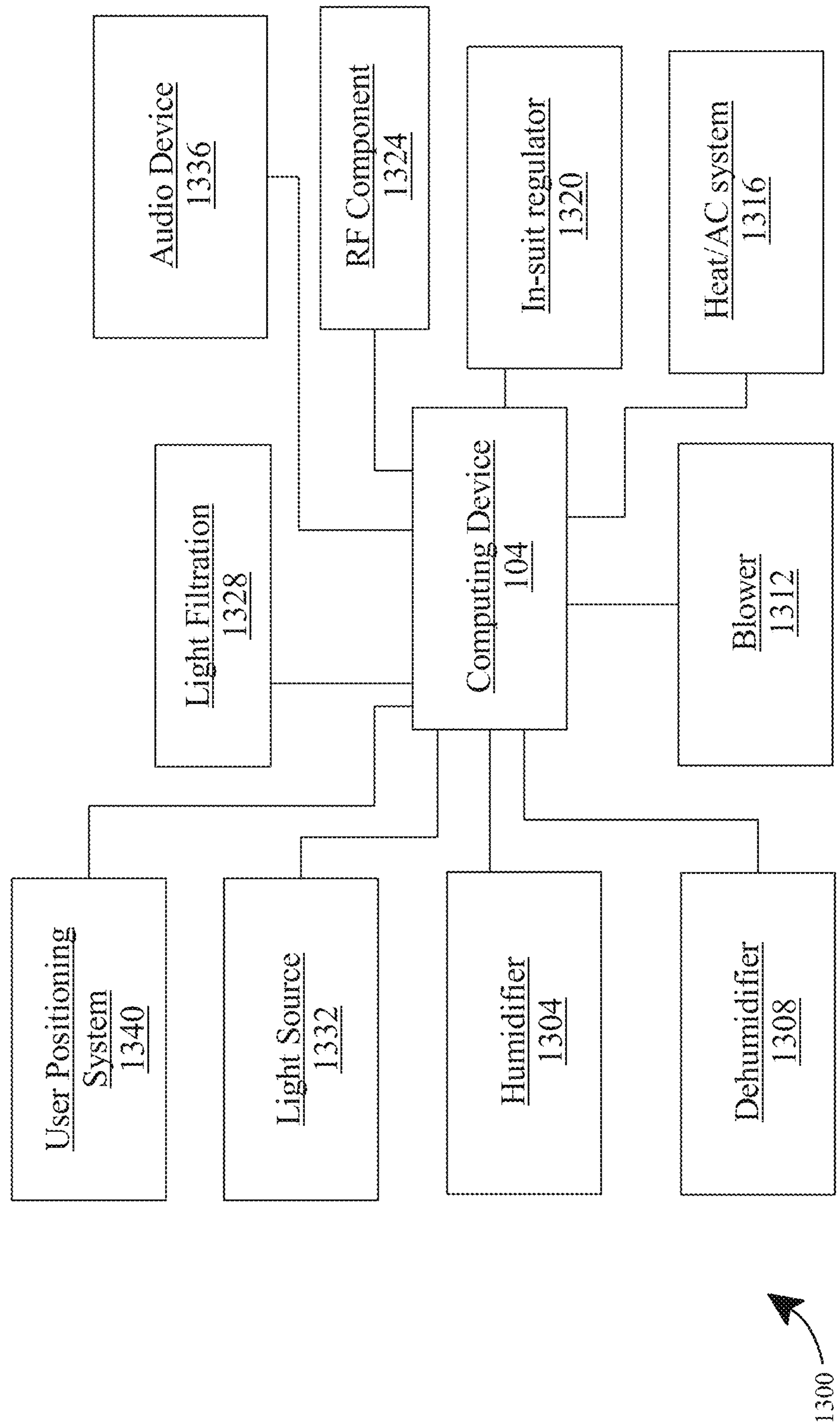
FIG. 13 is a block diagram illustrating exemplary embodiments of systems and/or components for modulation of environmental parameters.

Referring now to FIG. 13, an exemplary embodiment of an assembly for modification of environmental parameters is illustrated. Computing device 104 may direct one or environmental components 1300 to modify one or more environmental parameters as described above. An "environmental component" as used in this disclosure is a device and/or component that a computing device can direct and/or command to modify an environmental parameter, which may include any environmental parameter as described above. Environmental components 1300 may include any components, devices, and/or elements for affecting and/or modifying environmental parameters that may occur to a person skilled in the art upon reviewing the entirety of this disclosure. Modification of an environmental parameter may include modification thereof within a room and/or enclosure containing a person, and/or modification at the person through mediation of a wearable device, suit, helmet, headset, or the like, as will be further elucidated by the following exemplary embodiments. Computing device may determine, for each such environmental component 1300, an output command directing the component 1300 to modify the environmental parameter. Such output may be generated by a machine-learning model and/or fuzzy inferencing system as described above; training data for machine-learning model may, for instance, correlate biofeedback signals and/or combinations of biofeedback signals with measurements of environmental parameters to an exemplary and/or desired output to an environmental component 1300, and be used to train a machine-learning model that inputs biofeedback signals and generates outputs to environmental components 1300. Such training data may be used to train and/or tune parameters of a fuzzy inferencing system that produces outputs from such biofeedback signals and/or measurements, for instance by combining linguistic variable values representing biofeedback signals with linguistic variable values representing environmental measurements and/or other biofeedback signals using one or more inferencing rules to output a functional output, a defuzzified output, or the like controlling one or more environmental components 1300. Alternatively, computing device may use machine-learning models and/or inferencing systems as above to generate modifications and/or intended modifications to environmental parameters, which modifications may be input to additional machine-learning models and/or fuzzy inferencing systems that input modifications and generate outputs to environmental components 1300. Training data for a machine-learning model may, for instance, correlate modifications, potentially in combination with measurements of environmental parameters, to an exemplary and/or desired output to an environmental component 1300, and be used to train a machine-learning model that inputs modifications and/or environmental parameter measurements and generates outputs to environmental components 1300. Such training data may be used to train and/or tune parameters of a fuzzy inferencing system that produces outputs from such modifications and/or environmental measurements, for instance by combining linguistic variable values representing modifications with linguistic variable values representing environmental measurements and/or other modifications using one or more inferencing rules to output a functional output, a defuzzified output, or the like controlling one or more environmental components 1300. Outputs may include commands to switch such device on or off for some period of time, and/or may be managed by a closed-loop control system that compares environmental parameters to goal parameters, generates an error function, and modifies output iteratively to converge on a desired value for one or more parameters. Control system may include a second, outer loop determining a change in biofeedback, comparing the determined change to a goal change, generating an error function, and modifying an inner-loop environmental parameter goal and/or output as a result; such modification may include any process for output generation as described in this disclosure, and may be based on environmental parameter measurements as well as biofeedback.

As a non-limiting example, and still referring to FIG. 3, environmental components 1300 may include components to modify humidity. Such components may include a humidifier 1304, which may include any humidifier such as without limitation a wick or evaporation-based humidifier, a boiler and/or evaporator humidifier, an ultrasonic humidifier, or the like. Environmental components to affect humidity may include, without limitation, dehumidifiers 1308, which may function using by cycling air past a cooling source, such as, in an aircraft, a heat exchanger that dissipates heat to an exterior of the aircraft; alternatively or additionally, dehumidifier 1308 may use one or more cooling systems and/or coils such as condenser-based cooling as in an air conditioning system or the like. Outputs to a humidifier 1304 and/or dehumidifier 1308 may include commands to switch such device on or off for some period of time, and/or may be managed by a closed-loop control system that compares environmental parameters to goal parameters, generates an error function, and modifies output iteratively to converge on a desired value for one or more parameters, for instance and without limitation as described above.

With continued reference to FIG. 3, environmental components 1300 may include one or more blowers 1312 to modify and/or direct airflow. Blowers may include fans, impellers, and/or other devices that generate airflow, valves, gates, flaps or the like to redirect airflow, and/or any other devices and/or components to generate and/or redirect airflow, including a device to move a device that generates airflow about on a swivel and/or bearing, which may be motorized. Outputs to a blower 1312 and/or component thereof may include commands to switch such device on or off for some period of time, to modify a position and/or state of a gate, flap, valve, or other redirection component, or the like, and/or may be managed by a closed-loop control system that compares environmental parameters to goal parameters, generates an error function, and modifies output iteratively to converge on a desired value for one or more parameters, for instance and without limitation as described above.

Still referring to FIG. 13, environmental components 1300 may include a heat and/or air conditioning system 1316 to modify temperature within a room and/or chamber, and/or an in-suit regulator 1320 to modify temperature immediately about a person and/or within a suit worn thereby. For instance, and without limitation, air may flow past a heat exchanger, a heat source such as without limitation a resistive heater, and/or a compressor, to heat up and/or cool down the air. An in-suit heating or cooling system 1320 may include without limitation a system that cycles liquid or other fluid through tubing within a suit, which liquid and/or fluid may be warmed or cooled to produce a desired effect on body temperature. Outputs to a heat and/or air conditioning system 1316 and/or to an in-suit regulator 1320 may include commands to switch such device on or off for some period of time, and/or may be managed by a closed-loop control system that compares environmental parameters to goal parameters, generates an error function, and modifies output iteratively to converge on a desired value for one or more parameters, for instance and without limitation as described above.

With continued reference to FIG. 13, environmental components may include radiofrequency components 1324, which may include any components that emit and/or receive radiofrequency signals; such components may act to modify, filter, augment, and/or reduce such signals, for instance by canceling and/or jamming an incoming signal, by muting or reducing a transmitted signal, or the like. Outputs to radiofrequency components 1324 may include commands to switch such device on or off for some period of time, and/or may be managed by a closed-loop control system that compares environmental parameters to goal parameters, generates an error function, and modifies output iteratively to converge on a desired value for one or more parameters, for instance and without limitation as described above.

Still referring to FIG. 13, environmental components 1300 may include one or more light filtration 1328 components and/or light sources 1332, for altering visible light, ultraviolet light, infrared light, and/or other electromagnetic radiation. Alterations to such light and/or radiation may include reduction in intensity. Alterations may include suppression and/or augmentation of radiation within a specified spectrum, such suppression of infrared radiation to lower temperature in a cabin and/or at a person, suppression of ionizing frequencies, and/or shifts in visible frequency spectra; for instance, a "warmer" visible light with less higher-frequency blue and/or violet light may aid a person in becoming calmer and/or prevent eye strain, while a more "blue-shifted" visible light output may increase alertness. Modifications may alternatively or additionally include blocking specific frequencies, for instance, a "bandstop" or "antinotch" filtration approach may be used to eliminate unpleasant or distracting signal in an identified frequency, frequency range, and/or set of frequencies. A filtration device 1328 may accomplish any such results by filtering light at goggles, windows, and/or other transparent surfaces between a light source and a person's eyes; such filters may include static optical filters which may be swapped with one another to achieve different effects, and/or electrically and/or acoustically controlled devices. An example of the latter may include electrochromic and/or electronchromatic devices, which may be constructed of two or more electrochromatic layers separated by an electrolytic layer. Such devices may be regulated using an external voltage, with conducting electrodes used on ither side of both EC layers. Electrochromic devices may be categorized as Laminated employing a which liquid gel is employed as an electrolyte, and solid-state devices in which solid inorganic or organic material such as without limitation $Ta_2O_5$ and $ZrO_2$ is used as the electrolyte. An electrochromic device may include, as a non-limiting illustration, five superimposed layers on one substrate or positioned between two substrates in a laminated configuration: an electrochromatic layer and ion-storage layer may conduct ions and electrons, an electrolyte may function as a pure ion conductor and separate two EC layers. A transparent conductor may act as a pure electron conductor. Optical absorption may occur when electrons move into electrochromatic layers from transparent conductors along with charge balancing ions entering from electrolyte layers. Persons skilled in the art, having the benefit of the entirety of this disclosure, will be aware of various alternative or additional light filtration devices that may be employed. Light filtration devices may act to filter and/or modified external and/or natural light, as well as artificial and/or ambient light.

Still referring to FIG. 13, light source 1332 may use any filtration devices as described above, as well as other devices such as reflective and/or refractive gratings to modify intensity overall or at various frequencies in visible and/or other light. Alternatively or additionally, light sources 1332 may include abilities to vary output frequencies by modifying intensity of one or more luminous pixels and/or point sources in a monitor screen and/or other light source, and/or by modification of specific pixels in a variable-frequency light-emitting diode (LED) and/or organic LED (OLED) or the like. Outputs to a light filtration device 1328 and/or light source 1332 may include commands to switch such device on or off for some period of time, to modulate such device in any way described above, and/or may be managed by a closed-loop control system that compares environmental parameters to goal parameters, generates an error function, and modifies output iteratively to converge on a desired value for one or more parameters, for instance and without limitation as described above.

With continued reference to FIG. 13, environmental components 1300 may include one or more audio devices 1336. Audio devices may include, without limitation speakers or other audio output devices, noise-cancellation devices such as noise-canceling headsets, and/or any other devices capable of generating, suppressing, and/or redirecting sound. Audio devices 1336 may be employed to modify sound level and/or characteristics, including changes to actual or perceived overall volume. Audio devices 1335 may modify a noise profile, for instance by boosting or suppressing one or more sound frequencies; as a non-limiting example, if biofeedback indicates a high stress level, a relative increase in low-frequency noise may be produced to create a calming effect, whereas lower-frequency sound may be reduced and/or suppressed to increase alertness. In some embodiments, audio device 1336 may act to block specific frequencies; for instance a "bandstop" or "antinotch" filtration approach may be used to eliminate unpleasant or distracting noise in an identified frequency, frequency range, and/or set of frequencies. Audio device 1336 may alternatively or additional block noise having particular profiles, such as Gaussian noise, random noise, or the like. Outputs to an audio device 1336 may include commands to switch such device on or off for some period of time, commands to modulate such device to block, suppress, and/or modify sound, and/or commands that may be managed by a closed-loop control system that compares environmental parameters to goal parameters, generates an error function, and modifies output iteratively to converge on a desired value for one or more parameters, for instance and without limitation as described above.

With continued reference to FIG. 13, environmental components 1300 may include a user position system 1340. As used in this disclosure, a "user positioning system" is a system which affects a user's position. Exemplary user positioning systems include without limitation mechanized chairs, seats, beds, and the like. In some cases, a user positioning system 1340 may control a pose of a user. For instance, a user may be seated within a chair which may be controlled according to an environmental parameter, such as without limitation seating angle, neck angle, and the like. A user positioning system may also include a system which instructs a user to change position. For instance, a user positioning system may instruct through an audio and/or visual communication that a user should "stand up straight," "look up," or the like. In some cases, a user positioning system 1340 may include a mechanism which compels movement of a user into a desired position, for instance with a robotic arm, tilting floor, or the like.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 14:
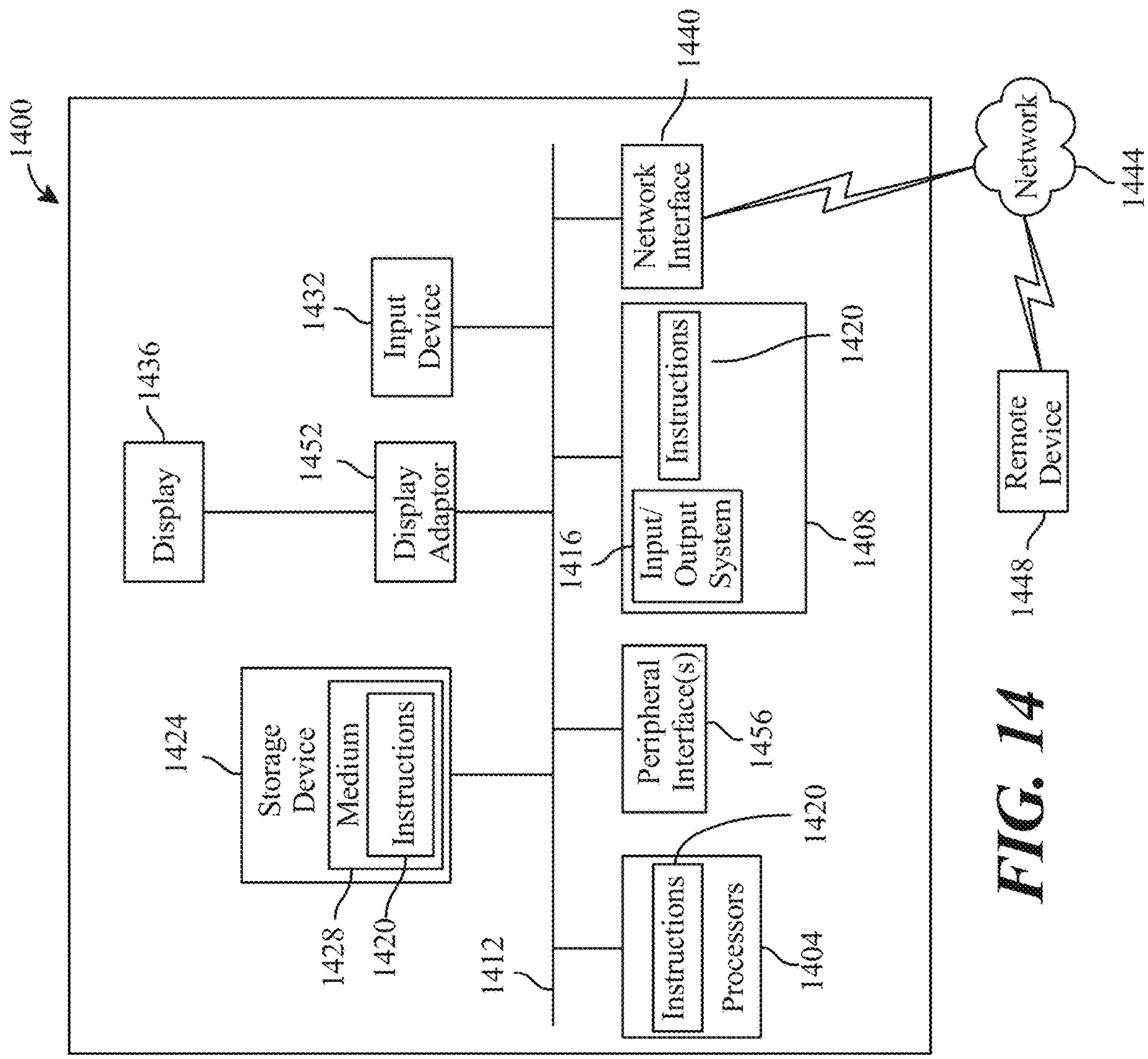
FIG. 14 is a block diagram of a computing system that can be used to implement any one or more of the methodologies disclosed herein and any one or more portions thereof.

FIG. 14 shows a diagrammatic representation of one embodiment of a computing device in the exemplary form of a computer system 1400 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1400 includes a processor 1404 and a memory 1408 that communicate with each other, and with other components, via a bus 1412. Bus 1412 may include any of several types of bus structures including, but not limited to, a memory bus, a memory controller, a peripheral bus, a local bus, and any combinations thereof, using any of a variety of bus architectures.

Processor 1404 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1404 may be organized according to Von Neumann and/or Harvard architecture as a non-limiting example. Processor 1404 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 1408 may include various components (e.g., machine-readable media) including, but not limited to, a random-access memory component, a read only component, and any combinations thereof. In one example, a basic input/output system 1416 (BIOS), including basic routines that help to transfer information between elements within computer system 1400, such as during start-up, may be stored in memory 1408. Memory 1408 may also include (e.g., stored on one or more machine-readable media) instructions (e.g., software) 1420 embodying any one or more of the aspects and/or methodologies of the present disclosure. In another example, memory 1408 may further include any number of program modules including, but not limited to, an operating system, one or more application programs, other program modules, program data, and any combinations thereof.

Computer system 1400 may also include a storage device 1424. Examples of a storage device (e.g., storage device 1424) include, but are not limited to, a hard disk drive, a magnetic disk drive, an optical disc drive in combination with an optical medium, a solid-state memory device, and any combinations thereof. Storage device 1424 may be connected to bus 1412 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1424 (or one or more components thereof) may be removably interfaced with computer system 1400 (e.g., via an external port connector (not shown)). Particularly, storage device 1424 and an associated machine-readable medium 1428 may provide nonvolatile and/or volatile storage of machine-readable instructions, data structures, program modules, and/or other data for computer system 1400. In one example, software 1420 may reside, completely or partially, within machine-readable medium 1428. In another example, software 1420 may reside, completely or partially, within processor 1404.

Computer system 1400 may also include an input device 1432. In one example, a user of computer system 1400 may enter commands and/or other information into computer system 1400 via input device 1432. Examples of an input device 1432 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1432 may be interfaced to bus 1412 via any of a variety of interfaces (not shown) including, but not limited to, a serial interface, a parallel interface, a game port, a USB interface, a FIREWIRE interface, a direct interface to bus 1412, and any combinations thereof. Input device 1432 may include a touch screen interface that may be a part of or separate from display 1436, discussed further below. Input device 1432 may be utilized as a user selection device for selecting one or more graphical representations in a graphical interface as described above.

A user may also input commands and/or other information to computer system 1400 via storage device 1424 (e.g., a removable disk drive, a flash drive, etc.) and/or network interface device 1440. A network interface device, such as network interface device 1440, may be utilized for connecting computer system 1400 to one or more of a variety of networks, such as network 1444, and one or more remote devices 1448 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 1444, may employ a wired and/or a wireless mode of communication. In general, any network topology may be used. Information (e.g., data, software 1420, etc.) may be communicated to and/or from computer system 1400 via network interface device 1440.

Computer system 1400 may further include a video display adapter 1452 for communicating a displayable image to a display device, such as display device 1436. Examples of a display device include, but are not limited to, a liquid crystal display (LCD), a cathode ray tube (CRT), a plasma display, a light emitting diode (LED) display, and any combinations thereof. Display adapter 1452 and display device 1436 may be utilized in combination with processor 1404 to provide graphical representations of aspects of the present disclosure. In addition to a display device, computer system 1400 may include one or more other peripheral output devices including, but not limited to, an audio speaker, a printer, and any combinations thereof. Such peripheral output devices may be connected to bus 1412 via a peripheral interface 1456. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A method of individualized content media delivery, the method comprising:

detecting, using at least a sensor, at least a biofeedback signal as a function of a biofeedback of a user;

presenting, using at least a display, content to the user; and controlling, using at least a computing device, at least an environmental parameter for an environment of the user as a function of the at least a biofeedback signal, wherein controlling the at least an environmental parameter further comprises:

generating an environmental machine-learning model as a function of an environmental machine-learning algorithm;

training the environmental machine-learning model as a function of an environmental training set, wherein the environmental training set comprises biofeedback inputs correlated to environmental parameter outputs; and generating an output to an environmental component as a function of the at least a biofeedback signal and the environmental machine-learning model; and communicating, using the at least a computing device, a communication metric, wherein the communication metric comprises feedback characterizing quality of communication with the user.

2. The method of claim 1, further comprising:

controlling, using the at least a computing device, at least a display parameter for the at least a display as a function of the at least a biofeedback signal, wherein controlling the at least a display parameter further comprises:

generating a display machine-learning model as a function of a display machine-learning algorithm;

training the display machine-learning model as a function of a display training set, wherein the display training set comprises biofeedback inputs correlated to display parameter outputs; and generating the at least a display parameter as a function of the at least a biofeedback signal and the display machine-learning model.

3. The method of claim 2, wherein the at least a display comprises an audio-visual display.

4. The method of claim 3, wherein the at least a display parameter comprises an audio parameter.

5. The method of claim 2, wherein the at least a display parameter comprises a speed of presentation for the content.

6. The method of claim 1, wherein the at least an environmental parameter comprises a thermal parameter.

7. The method of claim 1, wherein the at least an environmental parameter comprises a lighting parameter.

8. The method of claim 1, further comprising:

classifying, using the at least a computing device, a user state as a function of the at least a biofeedback signal, wherein classifying the state of the user further comprises:

generating a user state classifier as a function of a user state machine-learning algorithm;

training the user state classifier as a function of a user state training set; and classifying the user state as a function of the user state classifier and the biofeedback signal;

wherein generating the at least an environmental parameter further comprises selectively generating the at least an environmental parameter as a function of the user state.

9. The method of claim 8, wherein the user state is associated with attentiveness.

10. The method of claim 8, further comprising:

generating, using the at least a computing device, a confidence metric associated with classifying the user state.

11. A system for individualized content media delivery, the system comprising:

at least a sensor configured to detect at least a biofeedback signal as a function of a biofeedback of a user;

at least a display configured to present content to the user; and at least a computing device configured to control at least an environmental parameter for an environment of the user as a function of the at least a biofeedback signal, wherein controlling the at least an environmental parameter further comprises:

generating an environmental machine-learning model as a function of an environmental machine-learning algorithm;

training the environmental machine-learning model as a function of an environmental training set, wherein the environmental training set comprises biofeedback inputs correlated to environmental parameter outputs; and generating an output to an environmental component as a function of the at least a biofeedback signal and the environmental machine-learning model; and communicating a communication metric, wherein the communication metric comprises feedback characterizing quality of communication with the user.

12. The system of claim 11, wherein the computing device is further configured to control at least a display parameter for the at least a display as a function of the at least a biofeedback signal, wherein controlling the at least a display parameter further comprises:

generating a display machine-learning model as a function of a display machine-learning algorithm;

training the display machine-learning model as a function of a display training set, wherein the display training set comprises biofeedback inputs correlated to display parameter outputs; and generating the at least a display parameter as a function of the at least a biofeedback signal and the display machine-learning model.

13. The system of claim 12, wherein the at least a display comprises an audio-visual display.

14. The system of claim 13, wherein the at least a display parameter comprises an audio parameter.

15. The system of claim 12, wherein the at least a display parameter comprises a speed of presentation for the content.

16. The system of claim 11, wherein the at least an environmental parameter comprises a thermal parameter.

17. The system of claim 11, wherein the at least an environmental parameter comprises a lighting parameter.

18. The system of claim 11, further comprising:

classifying, using the computing device, a user state as a function of the at least a biofeedback signal, wherein classifying the user state further comprises:

generating a user state classifier as a function of a user state machine-learning algorithm;

training the user state classifier as a function of a user state training set; and classifying the user state as a function of the user state classifier and the biofeedback signal;

wherein generating the at least an environmental parameter further comprises selectively generating the at least an environmental parameter as a function of the user state.

19. The system of claim 18, wherein the user state is associated with attentiveness.

20. The system of claim 18, wherein the computing device is further configured to generate a confidence metric associated with classifying the user state.

* * * * *